(12) United States Patent
Rösch et al.

(10) Patent No.: US 10,130,722 B2
(45) Date of Patent: Nov. 20, 2018

(54) BIFUNCTIONAL CHELATING AGENTS BASED ON THE 1,4-DIAZEPINE SCAFFOLD (DAZA) FOR NON-INVASIVE MOLECULAR IMAGING

(71) Applicant: JOHANNES GUTENBERG-UNIVERSITÄT MAINZ, Mainz (DE)

(72) Inventors: Frank Rösch, Zornheim (DE); Bradley Peter Waldron, Thornaby (GB); David Parker, Durham (GB)

(73) Assignee: Johannes Gutenberg-Universität Mainz, Mainz (DE)

(*) Notice: Subject to any disclaimer, the term of this patent is extended or adjusted under 35 U.S.C. 154(b) by 0 days.

(21) Appl. No.: 14/897,142

(22) PCT Filed: May 14, 2014

(86) PCT No.: PCT/EP2014/059874
§ 371 (c)(1),
(2) Date: Dec. 9, 2015

(87) PCT Pub. No.: WO2014/198478
PCT Pub. Date: Dec. 18, 2014

(65) Prior Publication Data
US 2016/0136309 A1   May 19, 2016

(30) Foreign Application Priority Data
Jun. 11, 2013   (DE) .................. 10 2013 106 066

(51) Int. Cl.
A61K 51/04 (2006.01)
(52) U.S. Cl.
CPC ...... A61K 51/0482 (2013.01); A61K 51/0489 (2013.01)
(58) Field of Classification Search
CPC .............................. A61K 49/00; A61K 51/04
See application file for complete search history.

(56) References Cited

U.S. PATENT DOCUMENTS

| | | | |
|---|---|---|---|
| 7,186,400 B2 | 3/2007 | Giovenzana et al. | |
| 7,893,223 B2* | 2/2011 | Giovenzana ....... | A61K 49/0002 534/10 |
| 2006/0034773 A1 | 2/2006 | Giovenzana et al. | |
| 2010/0166656 A1* | 7/2010 | Campa .................. | C07H 23/00 424/9.1 |

OTHER PUBLICATIONS

Silvio Aime et al. An unusal gadolinium ten-coordinated dimeric complex in the series of MRI contrast agents: Na[Gd(H2O)AAZTA]. 3H2O, Inorganica Chimica Acta, 2008, 361, 1534-1541.*
Leonardo Manzoni et al. Synthesis of Gd and 68Gd Complexes in Conjugation with a Conformationally Optimized RGD Sequence as Potential MRI and PET Tumor-Imaging Probes, ChemMedChem, 2012, 7, 1084-1093.*
Müller, P., "Glossary of Terms Used in Physical Organic Chemistry (IUPAC Recommendations 1994)," *Pure & Applied Chemistry*, 1994, vol. 66, No. 5, pp. 1077-1184.
Johanna, Seemann, et al., "Novel Ga-68-labeled folic acid derivatives," *Journal of Labelled Compounds and Radiopharmaceuticals*, May 2013, vol. 56 No. Suppl. 1, p. S351.
Manzoni, Leonardo, et al., "Synthesis of Gd and 68 Ga Complexes in Conjugation with a Conformationally Optimized RGD Sequence as Potential MRI and Pet Tumor-Imaging Probes," *Chemmedchem*, Jun. 5, 2012, vol. 7, No. 6, pp. 1084-1093.
Parker, David, et al., "Crystallographic and solution NMR structural analyses of four hexacoordinated gallium(III) complexes based on ligands derived from 6-amino-perhydro-1,4-diazepine," *Dalton Transactions*, May 2013, pp. 8001-8008.
Parker, David, et al., "Conformational analysis and synthetic approaches to polydentate perhydro-diazepine ligands for the complexion of gallium(iii)." *Organic & Biomolecular Chemistry*, Jan. 1, 2013, vol. 11, No. 17, p. 2827.
Tei, Lorenzo, et al., "Mn(ii) complexes of novel hexadentate AAZTA-like chelators: a solution thermodynamics and relaxonmetric study," *Dalton Transactions*, Jan. 1, 2011, vol. 40, No. 9, p. 2025.

(Continued)

*Primary Examiner* — Michael G Hartley
*Assistant Examiner* — Jagadishwar Rao Samala
(74) *Attorney, Agent, or Firm* — ProPat, L.L.C.; Cathy R. Moore

(57) ABSTRACT

A compound for radio metal complexation includes a chelator and one or more biological targeting vectors TV conjugated to said chelator, wherein the chelator has structure (A) or (B) or (C),

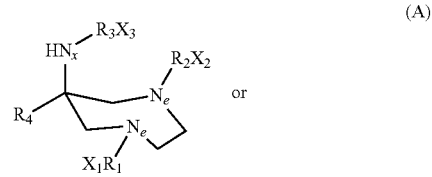
(A)

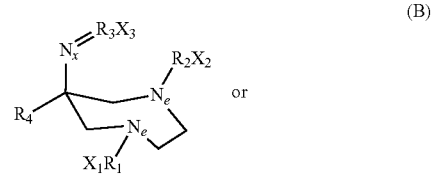

(B)

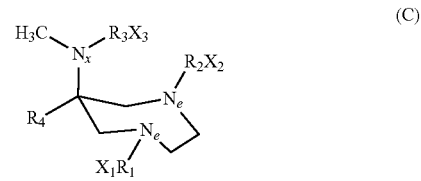

(C)

based on 1,4-diazepine with groups $R_1$, $R_2$, $R_3$, $R_4$, $X_1$, $X_2$, $X_3$. The compound is particularly suited for complexation of radio-isotopic metals, such as $^{66}$Ga(III), $^{67}$Ga(III) and $^{68}$Ga(III).

10 Claims, 10 Drawing Sheets

(56) References Cited

OTHER PUBLICATIONS

Waldron, Bradley P., et al., "Structure and stability of hexadentate complexes of ligands based on AAZTA for efficient PET labelling with gallium-68," *Chemical Communications*, Jan. 1, 2013, vol. 49, No. 6, p. 579.

* cited by examiner

BIFUNCTIONAL CHELATING AGENTS BASED ON THE 1,4-DIAZEPINE SCAFFOLD (DAZA) FOR NON-INVASIVE MOLECULAR IMAGING

CROSS-REFERENCE TO RELATED APPLICATIONS

This application is being filed under 35 U.S.C. § 371 as a National Stage Application of pending International Application No. PCT/EP2014/059874 filed May 14, 2014, which claims priority to the following parent application: German Patent Application No. 10 2013 106 066.8, filed Jun. 11, 2013. Both International Application No. PCT/EP2014/059874 and German Patent Application No. 10 2013 106 066.8 are hereby incorporated by reference herein in their entirety.

FIELD OF INVENTION

The present invention relates to chelating agents, to complexes of these chelating agents with radio-isotopic metal ions, and to conjugates of these chelating agents (bifunctional chelators: BFC's) with biological targeting vector or carrier molecules. More specifically, the invention relates to chelators and BFC's for radiometals ($^{66}$Ga, $^{67}$Ga and $^{68}$Ga in particular) which are useful for applications relating to therapy and diagnostic imaging.

BACKGROUND OF THE INVENTION

Radiopharmaceuticals with application in diagnostic imaging and therapy have important roles in modern medicine. For the most part, these radioisotopes are radiometals which are either main group metals or part of the lanthanide series. This family of radioisotopes possess a plethora of nuclear and chemical properties, which can be utilised in diagnostic and therapeutic applications. In addition, this family possess a number of advantages over their non-metal counterparts. For instance, radio-labelling using radiometals is typically the final synthetic step and through development and optimisation is usually high-yielding. Furthermore, certain radiometals can be produced conveniently and cost efficiently (within GMP requirements) by means of an on-site generator.

However, in nearly all cases the free (cationic) metal ions are inherently toxic with defined bio-distributions. In order to render these radiometals biologically applicable and useful the metal cations must be complexed by a suitable ligand (organic based chelator). Ligands can be used to 'shield' the metal ions from the environment which may otherwise compromise their intended use.

Whilst, the exact nature of the resulting complex (size, redox properties, donor groups, charge, size) will influence its biodistribution, it is widely acknowledged that in order to create a effective, useful and applicable biodistribution it is necessary to incorporate some form of targeting vector with the radio-label. One method for doing so involves the covalent attachment of the targeting vector, in some cases via a coupling unit, to the ligand. Compounds which possess both a chelating and targeting unit are commonly referred to as bifunctional chelators (BFC's).

The development of ligands for the complexation of main group and lanthanide metal ions has been a focus of research for many years, and driven for the most part by advances in medicine. For instance the development of magnetic resonance imaging (MRI) for diagnosis, initiated the development of contrast agents which enhance the image quality. For these applications, paramagnetic complexes of gadolinium in particular have proven effective and are preferred. As a consequence there has been considerable focus on the development of new ligands suitable for in vivo application. Due to the chemical similarity of metals in the lanthanide series, many of these ligands can be used with other lanthanide ions. Of particular interest in this regard are radio-nuclides such as $^{153}$Sm, $^{177}$Lu, $^{166}$Ho and $^{90}$Y (a 'lanthanide-like' radiometal), which are potentially useful as radiopharmaceuticals. This similarity within the lanthanide series has resulted in the emergence of a new field entitled THERANOSTICS (THERApy and diagNOSTICS). The premise is that once a ligand has been designed which works effectively as part of a complex in diagnostic imaging it could then, in theory, be applied in therapeutic applications simply be changing the metal radionuclide used.

In terms of metallo-radiopharmaceutical there are two critical pre-requisites which should be met, if they are intended for human use. Firstly, the radio-labelled complex should be stable in vivo over at least the intended application of the radiopharmaceutical. Secondly, due to the inherent time constraints arising from the half-life of the radionuclide of interest, radio-labelling should be efficient and fast. Therefore, the suitability of a BFC is evaluated in terms of its kinetic (and to a lesser extent it's thermodynamic) stability, and rate of radio-labelling. Whilst a high thermodynamic complex stability is desirable for in vivo application such complexes are typically more difficult to form, requiring longer reaction times and greater energy input.

Gallium is a main group metal with three radioisotopes which can be used in radiopharmaceuticals. $^{66}$Ga and $^{68}$Ga are positron emitters, with half-lives of 9.5 h and 67.7 min respectively, and $^{67}$Ga is a γ(gamma)-emitter with a half-life of 3.26 days. $^{68}$Ga represents one of the very early radio-nuclides applied in Positron Emission Tomography (PET). In recent times there has been somewhat of a renaissance of the $^{68}$Ga radionuclide, which is largely a result of the availability of the radionuclide from a cost effective and convenient generator. Modern generators are eluted using hydrochloric acid provide "cationic" $^{68}$Ga, as opposed to the "inert" $^{68}$Ga complexes extracted from previous generations. In addition to this $^{68}$Ga is favoured due to its chemical and radiochemical properties, which allow for the formation of sufficiently stable radio-labelled complexes with desirable radiochemical decay characteristics (high β$^+$-emission yield of 89%, suitable γ-ray energy, convenient half-life of 67.7 min).

Largely following the development of MRI and Single Photon Emission Computed Tomography (SPECT) imaging agents, the $^{68}$Ga cation was initially chelated using existing ligands. Namely; EDTA-(ethylenediamintetraacetic acid), DTPA-(diethylenetriaminepentacetic acid) or DOTA-(1,4,7,10-tetraazacyclododecane-1,4,7,10-tetraacetic acid) based derivatives (Figure I). The replacement of $^{111}$In-Octreoscan (DTPA with a coupled octreotide targeting vector) by $^{68}$Ga-DOTA-octreotides in clinical PET/CT imaging of neuroendocrine tumours, has paved the way not only for clinical acceptance of $^{68}$Ga-radiopharmceuticals, but also given recognition to the potential of the $^{68}$Ga/$^{68}$Ga radionuclide generator.

FIG. 1 Commonly used chelators, in their 'parent' form, for metal based imaging agents

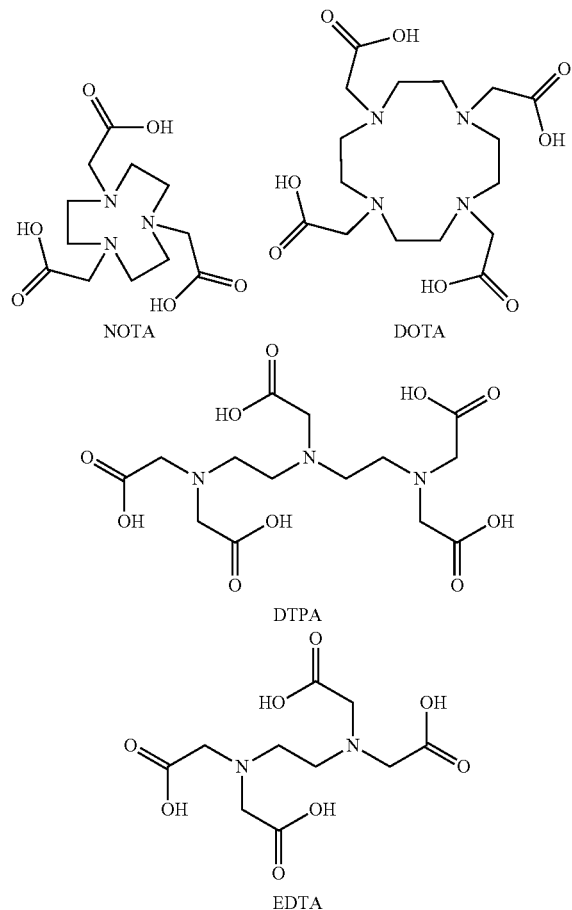

Ligands currently used to chelate $^{68}$Ga(III) and provide a means for attachment of a targeting vector are mostly derivatives of DOTA and NOTA (1,4,7-triazacyclononane-1,4,7-tricetic acid: Figure I). Whilst both ligands give rise to $^{68}$Ga radio-labelled complexes of exceptionally high stability, they possess inherent disadvantages. DOTA ligand derivatives in particular are not well-suited for $^{68}$Ga chelation; a feature which is manifested as the long reaction times and high temperatures required for radio-labelling.

The NOTA ligand derivatives are much better matched to the coordination requirements of $^{68}$Ga(III), which largely addresses these problems without detriment to the thermodynamic stability. However, NOTA derivatives are disadvantaged by the acidic pH conditions required for radio-labelling (which limits the biological targeting vectors which can be used), cost and difficult syntheses. Whilst they serve the purpose, improvements to increase efficiency, suitability, application and costs are required to realise the potential of the favourable $^{68}$Ga-radionuclide. Specific areas of improvement include quantitative radio-labelling at milder pH and lower temperatures, whilst maintaining sufficient in vivo stability. These improvements are important for the widespread use and development of $^{68}$Ga as the radionuclide of choice for PET/CT.

It is interesting to note that, with few exceptions, trends have seen a deviation away from rigid cyclic chelators (DOTA and NOTA) towards more flexible acyclic systems. Acyclic ligands are typically synthetically less challenging and tend to radio-label more rapidly; however the absence of the macrocyclic effect renders them kinetically less stable to metal dissociation.

In the last few years several acyclic and macrocyclic ligands have been reported, which are thought to have favourable properties for the chelation of $^{68}$Ga(III) (Figure II).

FIG. II Examples of ligands which provide potential for coupling of targeting vectors (indicated in red), and have $^{68}$Ga-radio-labelling properties considered favourable, i.e. fast radio-labelling with nearly quantitative yields.

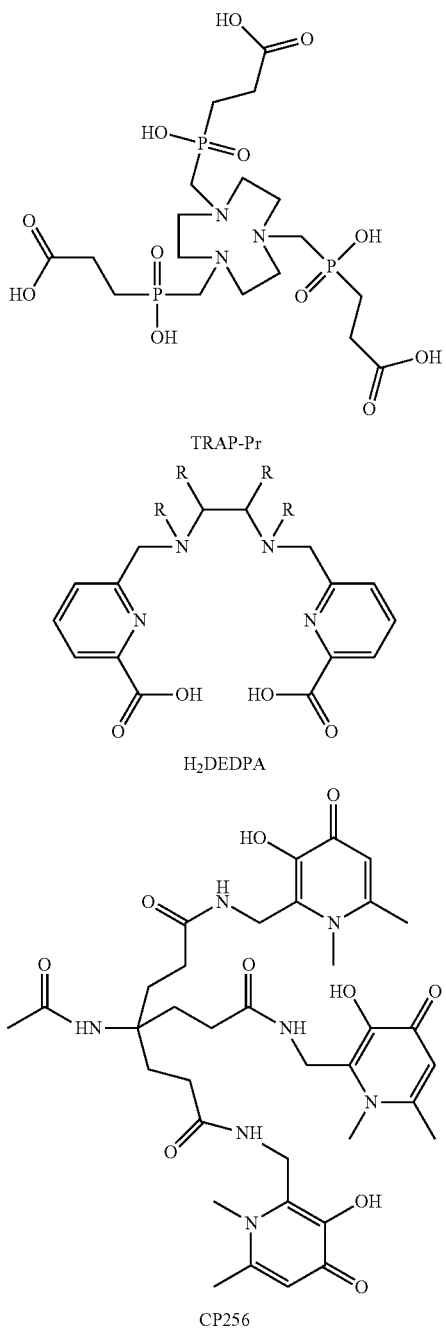

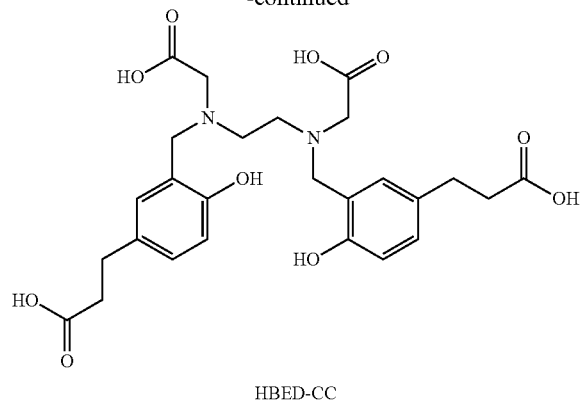

HBED-CC

Ideally ligands should radio-label with $^{68}$Ga(III) rapidly (<10 min) at mild pH and temperature. Furthermore they should provide a point/s of attachment of a targeting moiety, which are isolated from the inert chelating core, and be selective for $^{68}$Ga(III) over other metal cations such as iron(III).

At present $^{99m}$Tc radiopharmaceuticals can be prepared using a kit-type radio-labelling protocol, in which the lyophilised ligand (and other compounds required for labelling, such as a buffer) is contained in a vial to which the generator eluate is directly added to initiate the labelling. The $^{68}$Ge/$^{68}$Ga generator has a longer shelf life that the $^{99}$Mo/$^{99m}$Tc generator, and therefore the development of a similar kit-type radio-labelling protocol would be a considerable step towards the clinical application and widespread adoption of $^{68}$Ga radiopharmaceuticals. This requires the development of BFCs that label quantitatively and rapidly at room temperature, physiological pH, low BFC concentrations and in the presence of competing metal ions.

Ligands featuring the 1,4-diazepine (DAZA: Figure II) scaffold have been investigated in four main areas. These are as:

heptadentate ligands for complexes which may act as diagnostic (MRI and PET) imaging agents hexadentate ligands for manganese(II) complexes for potential application as contrast agents for MRI tetra- and penta-dentate ligands for potential application in rare earth metal catalysis tridentate ligands for transition metals Of particular relevance to this work are the complexes relating to imaging applications. There are currently two accepted patents (the second being a continuation of the first) which are related to the invention claimed here. A description encompassing this work, and related literature, is of relevance to this invention.

The compounds patented (U.S. Pat. No. 7,893,223 B2 and U.S. Pat. No. 7,186,400 B2) are defined by the structural formula shown in Figure III. The nature of the variable groups (FG and $Y_{1-5}$) is broad, and encompasses a wide range of chemical functionalities. $N_x$ designates the exocyclic nitrogen atom.

FIG. III General structure used for the description of ligands pertaining to the patents relevant to this field of research.

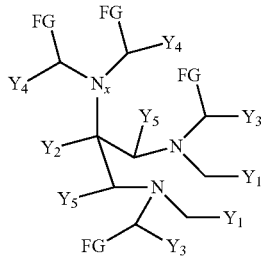

The variable groups (FG and $Y_{1-5}$) are defined by the following chemical functionalities:

In the instance of 1,4-diazepine derivatives, the $Y_1$ groups are taken together to form a straight or cyclic $C_2$-$C_{10}$ alkylene group, or an ortho-disubstituted arylene.

$Y_{2-5}$ are an H, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amine moiety, each of which may be further optionally substituted with functional groups selected from the group consisting of carboxyl, amino, aldehydes, haloalkyl, maleimidoalkyl, hydroxyl and sulphydryl groups which allow conjugation with a suitable molecule able to interact with physiological systems.

FG may be the same or different, are carboxy, —$PO_3H_2$ or —RP(O)OH, wherein R is hydrogen, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amine moiety, each of which may be further optionally substituted with functional groups selected from the group consisting of carboxyl, amino, aldehydes, haloalkyl, maleimidoalkyl, hydroxyl and sulphydryl groups which allow conjugation with a suitable molecule able to interact with physiological systems.

The vast majority of research which utilises the 1,4-diazepine scaffold (DAZA: Figure IV), and its derivatives, has focused on the chelation of paramagnetic metal ions and the use of the corresponding complexes as contrast agents for MRI. Complexes aimed at this application have comprised of a common chelating unit in which $Y_1$ is joined to form an ethylene bridge. All FG groups are carboxy, and $Y_{3-5}$ are hydrogens. The 'parent' ligand has $Y_2$ as a methyl group to give 6-amino-6-methzlperhydro-1,4-diazepineter-taacetic acid (AAZTA: Figure IV). The gadolinium(III) AAZTA complex displays favourable characteristics in terms of stability and relaxivity. The favourable relaxivity is consistent with the presence of two inner sphere coordinated water molecules and simultaneous favourable residence times of the coordinated water molecules. Derivatisation of this ligand to yield BFC's has focused exclusively on conjugation via $Y_2$. Some examples for AAZTA derivatives which have been used for the synthesis of BFC's and more complex structures are shown in Figure IV.

FIG. IV Structure of DAZA and AAZTA, and their derivatives which have been used for the synthesis of BFC's and more complex structures.

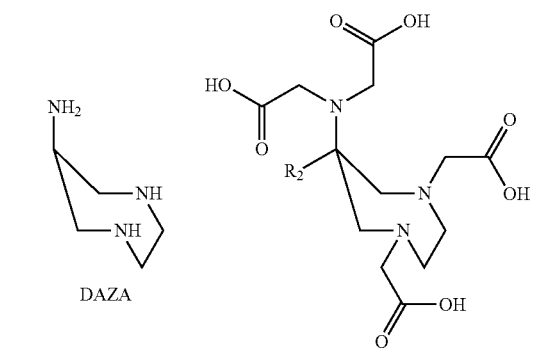

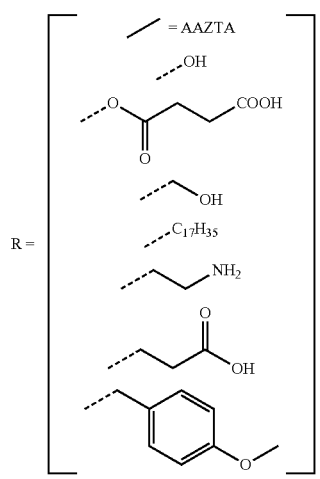

There are three examples in the literature of derivatives of the parent AAZTA ligand which included site modification other than $Y_2$. Botta et al investigated the usefulness of derivatives with reduced denticity, by replacing one of the FG groups (carboxy) with a coordinatively inert functioning group (Figure V). The resulting manganese complexes, sought as potential Mn(II) MRI contrast agents, were not sufficiently stable for application in vivo. Similar metal complex stabilities were echoed in the work of Hegetscheweiler which found that the functionalised triamine, 1,4-diazepine (DAZA), scaffold was poorly suited to the complexation of transition metal cations.

FIG. V AAZTA and hexadentate 'AAZTA-like' ligands synthesised by Botta et al (2011) as potential ligands for Mn(II) MRI contrast agents.

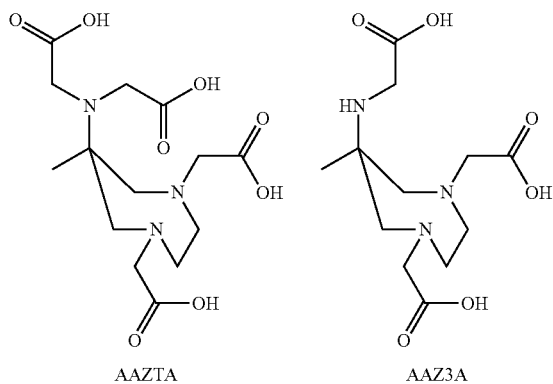

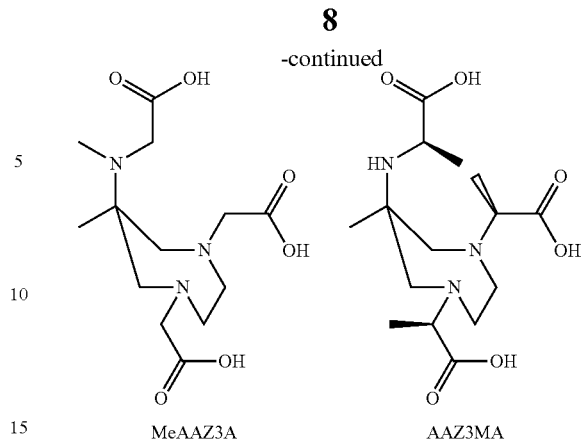

Parker and co-workers sought to modify the relaxivity of AAZTA derivatives, by functionalising one of the pendant acetate groups at $Y_3$ by the substitution of a proton for an alkyl carboxyl group (Figure VI). Subsequently, the suitability of the scaffold for use as lanthanide based fluorescent probes was investigated by replacing the endocyclic substituents ($R_3$ and connected FG) with sensitising chromophores (Figure VI). Neither derivatisation produced results which implored further development along these lines.

FIG. VI Modification of the AAZTA structure at the endocyclic amines. The diglutarate (left) and di-azaxanthone (right) derivatives of AAZTA. Conformations of the two chiral centres in the di-glutarate can be the same [(R,R) or (S,S)] or different [(S,R)].

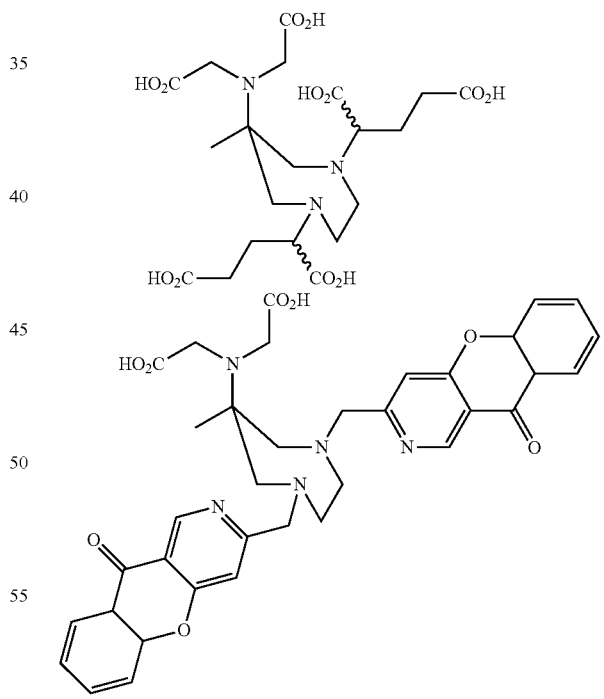

There is a single example in literature of a $^{68}$Ga complex featuring an AAZTA ligand (Figure VII). Binding affinity studies of the targeting vector with its receptor indicated that, AAZTA based BFC had the most detrimental effect on the binding affinity of the targeting vector (in comparison with BFC analogous of DTPA and DOTA analogues). Like all other examples, the targeting vector is attached to the chelating unit via $Y_2$.

FIG. VII The AAZTA ligand BFC derivative, AAZTA-DB58 used in $^{68}$Ga-radio-labelling and subsequent in vivo tumour model trails.

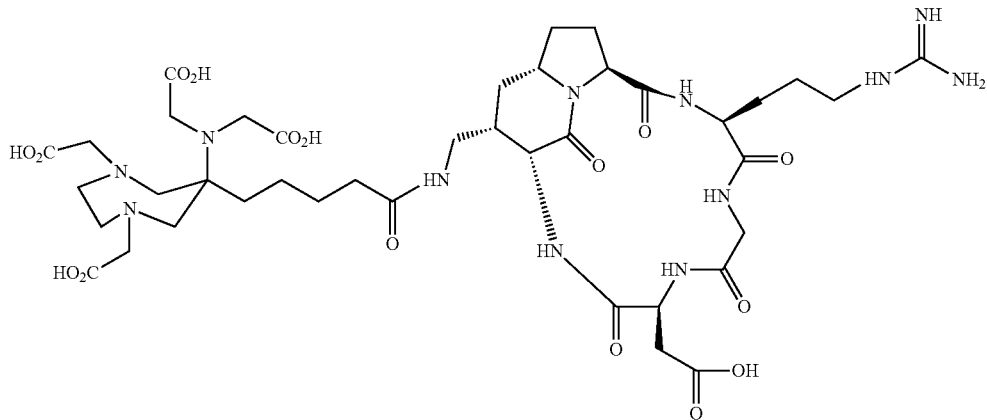

SUMMARY OF THE INVENTION

Crystal structures of lanthanide AAZTA complexes suggest that the lanthanide ion is too large for the binding cavity of the ligand, with approximately half of the metal ion exposed to the environment. It is evident from this observation, and the structural similarity of this ligand to NOTA, that it would be considerably better suited to a smaller metal ion. Furthermore, our results suggest that there is a strong case for minimizing substitution of the exocyclic amine. Consistent with this, increasing the steric demand of $Y_2$ close to the ring is also viewed as being beneficial. Of particular interest are complexes of the gallium isotopes (namely $^{66}$Ga, $^{67}$Ga, $^{68}$Ga and $^{71}$Ga). Gallium(III) prefers an octahedral coordination sphere of hard donor groups. For this purpose the AAZTA ligand coordination sphere is not ideal, and requires suitable modification.

Derivatisation of AAZTA at $Z_2$ is disclosed in the prior art; however these are limited to derivatives in which $Z_2$ is a $CH_2R$ moiety. Furthermore, there are no reported (or patented) examples of ligands which use the exocyclic amine and/or its pendant coordinating group as the point of attachment for the coupling unit. The invention encompasses complexes of ligands based on 1,4-diazepine with a nitrogen atom in the 6-position (the chelating unit) in which; each nitrogen atom of the scaffold has a single ligating group LG attached, and the chelating unit is attached to a targeting vector by means of a coupling unit. This gives preferred, but not limited to, ligands with a hexadentate coordination spheres. These ligands possess numerous possibilities for attachment of a coupling units (and by extension a targeting vector/s). In a preferred embodiment of the invention the ligand or chelator is defined by structure II:

STRUCTURE II

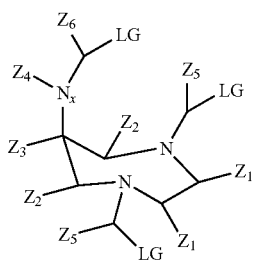

Structure II differs from known AAZTA-like chelators in that the exocyclic nitrogen ($N_x$):
  may have as one of its substituents a hydrogen atom;
  may be connected to the ring carbon via a double bond;
  and is not required to contain a carboxy, phosphinate or phosphinate based group in a defined position in relation to $N_x$.

Attachment of a coupling unit (and targeting vector) to the chelating unit occurs via $Z_3$, $Z_4$, and/or $Z_6$ in particular, with the option of also utilising $Z_1$, $Z_2$ and $Z_5$ for this purpose. $Z_3$ may take on a variety of chemical forms. In the instance where it is an aryl group, or a functionalised derivative thereof, $Z_4$ is hydrogen. In such examples the coupling unit (and targeting vector) is attached via optionally, or both, $Z_3$ and $Z_6$.

The invention pertains to a labelling precursor for a metallic radionuclide. The labelling precursor is a chelator and optionally comprises a targeting vector attached to the chelator. The chelator and/or BFC is a derivative of the DAZA scaffold, i.e. comprises a 1,4-diazepine seven membered ring functionalized at the nitrogen and carbon atoms of the ring and pendant amine substituents. The precursor is identified by the fact that it is built up from a chelate and a targeting vector which are connected via optional coupling or linker/spacer groups LS.

Preferably the precursors are defined according to structure II. The precursor respectively the chelator is labelled with a metallic radionuclide, preferably selected from $^{68}$Ga, $^{67}$Ga and $^{66}$Ga.

Particular embodiments of the invention are characterized in that:
  the 1,4-diazepine (DAZA) scaffold is functionalized and provides a means for attachment of a coupling unit;
  substituents $Z_{1-6}$ are hydrogen, carboxy, or optionally selected substituents and/or combinations of alkyl, aryl, acidic and amino groups. Each of these can also be further substituted or to provide means for attachment of a coupling or linker/spacer group LS;
  ligating groups LG, which are the same or different are chosen from carboxy, phosphonate, phosphinate, phenolate, hydroxamate and nitrogen based functional groups, each of which may be substituted/functionalised and/or provide means for attachment of a linker/spacer group LS;

the chelator is functionalized and provides means for attachment of a targeting vector via a linker/spacer group LS;

the one or more targeting vectors are coupled to the chelator by means of linker/spacer groups LS, which are attached to the chelating unit at $Z_{1-6}$, preferably at $Z_3$, $Z_4$ and/or $Z_6$;

the linker/spacer group LS is a residue of a linear, branched or heterosubstituted alkyl-, alkylene-, alkylidene-, aryl-, polyether- or polypeptide, which is coupled to the chelating moiety covalently;

the linker/spacer group LS is selected from aliphatic or aromatic amino- hydroxyl-, mercapto-, alkene, alkyne-, COOH-, CONH-, CNOH-, epoxy-, NCS-, COOH-, active ester, NCO-, COR-, B(OH)$_2$-, maleimide-, PR$_3$-, P(OR)$_3$-group, isothiocyanate/thiourea or analogical group (where R can be hydrogen or an alkyl-, alkylthio-, alkylamino-, alkylformamido-, aryl- or aryloxy-function);

the one or more targeting vectors, independently of one another, are selected from amino acids, bisphosphonates, sugars, purine- and pyrimidine bases, nucleotides, nucleosides and derivatives thereof, antibodies, antibody fragments, DNA-components, hypoxia tracers, cellular membrane compounds, glutamine, extra- or intracellular enzyme- or receptor ligands, which address the same or different biological targets;

the chelator is coupled to two or more different combinations of coupling units and targeting vectors;

the precursor comprises two or more of the above specified chelators;

the one or more targeting vectors are coupled to the chelator via optional spacer/linker groups LS at the exocyclic nitrogen ($N_x$) of the 1,4-diazepine (DAZA) scaffold either directly (i.e. substituting $Z_4$), or indirectly at the pendant arm covalently attached to the exocyclic amine (i.e. substituting $Z_6$);

the one or more targeting vectors are coupled to the chelator via optional spacer/linker groups LS at $Z_3$ (i.e. substituting $Z_3$);

radiolabelling of the precursor can be carried out in the presence of other metal cations such as iron(II), calcium(II) and copper (II);

radio-labelling of the precursor is carried out employing a solution at a pH-value from 2.3 to 7;

radio-labelling is carried out at low concentration of the precursor;

radio-labelling is carried out at a temperature from 20° C. to 90° C.;

radio-labelling is completed within a time interval of 6 s to 10 min, i.e. that, depending on the molar ratio of precursor molecules to radio-isotopic metal ions, more than 90 mol-% of either the precursor molecules or the radio-isotopic metal ions have been ligated;

radio-labelling is carried out in presence of other components such as buffers and anionic compounds; and/or the radio-labelled precursor, i.e. a complex formed by ligation of the precursor with a radio-isotopic metal ion, are stable over a period of two hours in the presence of chemical substances, such as apo-transferrin, DTPA, 1,4,7-triazacyclononane-1,4,7-triacetate (NOTA), serum and iron(III), at physiological pH from 7.0 to 7.8 and a temperature from 30° C. to 40° C.

DETAILED DESCRIPTION OF THE INVENTION

Figure 1:
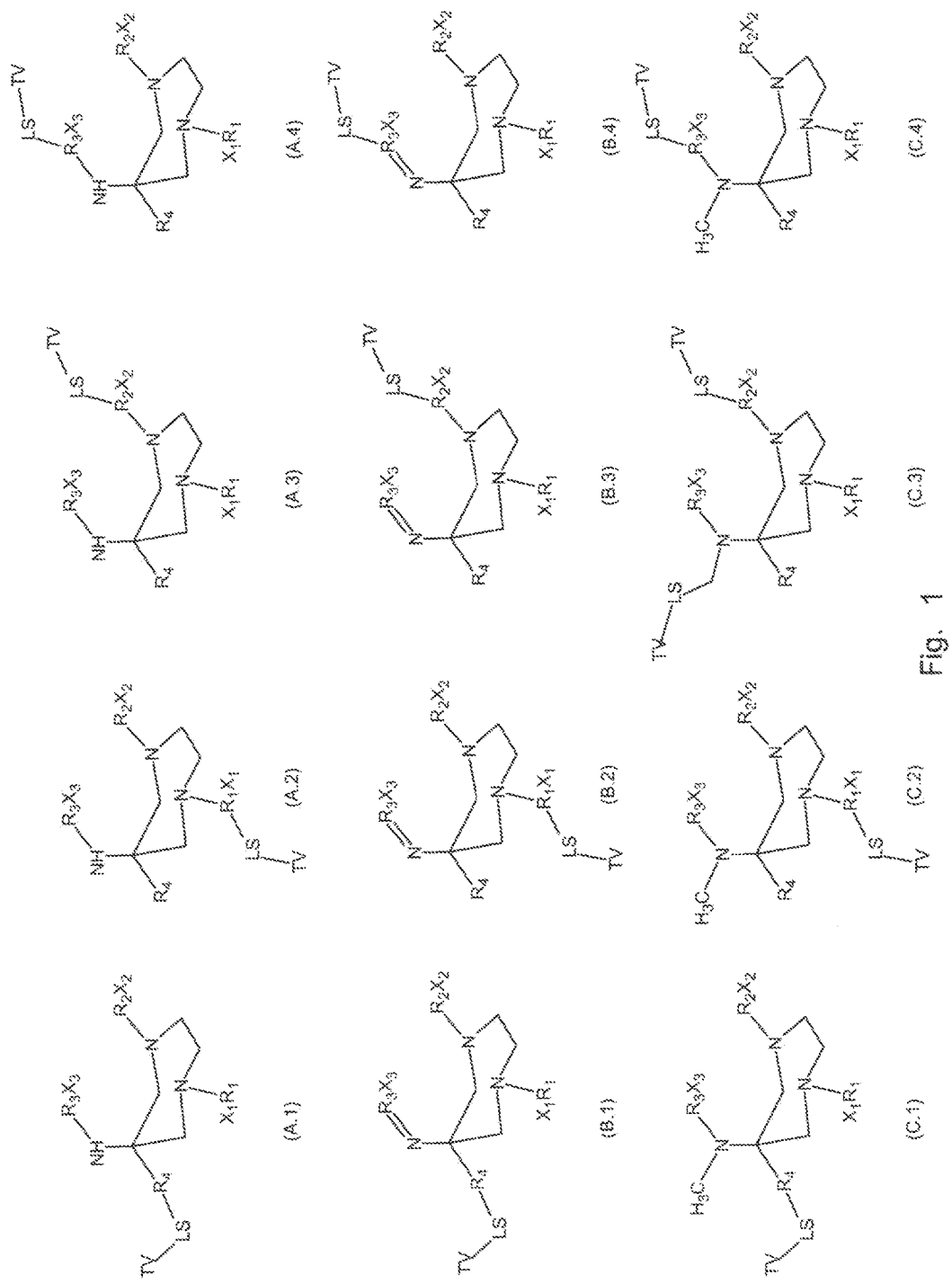
FIG. 1 shows embodiments of the inventive compound C according to general structures (A.1) to (A.4), (B.1) to (B.4) and (C.1) to (C.4) with a targeting vector TV attached at either of groups $R_1$, $R_2$, $R_3$, $R_4$ or at the methyl residue at the exocyclic nitrogen atom $N_x$.
Figure 2:
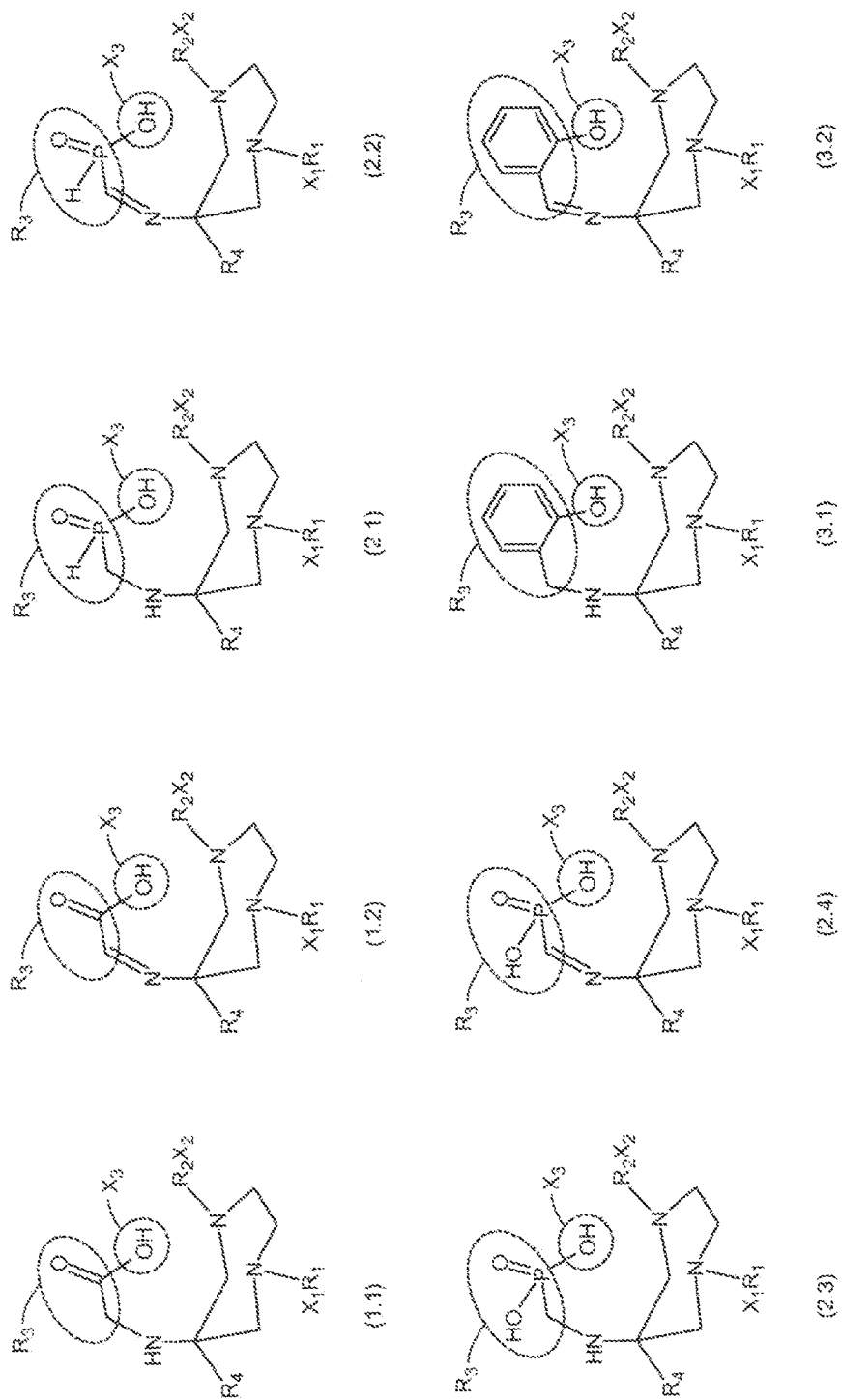
FIGS. 2 through 5 show embodiments of the chelator of the inventive compound C according to structures (1.1) to (1.2), (2.1) to (2.4), (3.1) to (3.6), (4.1) to (4.2), (5.1) to (5.4), (6.1) to (6.2), (7.1) to (7.4), (8.1) to (8.2), (9.1) to (9.2), (10.1) to (10.2) and (11.1) to (11.2) with various groups $R_3$ and $X_3$.
Figure 3:
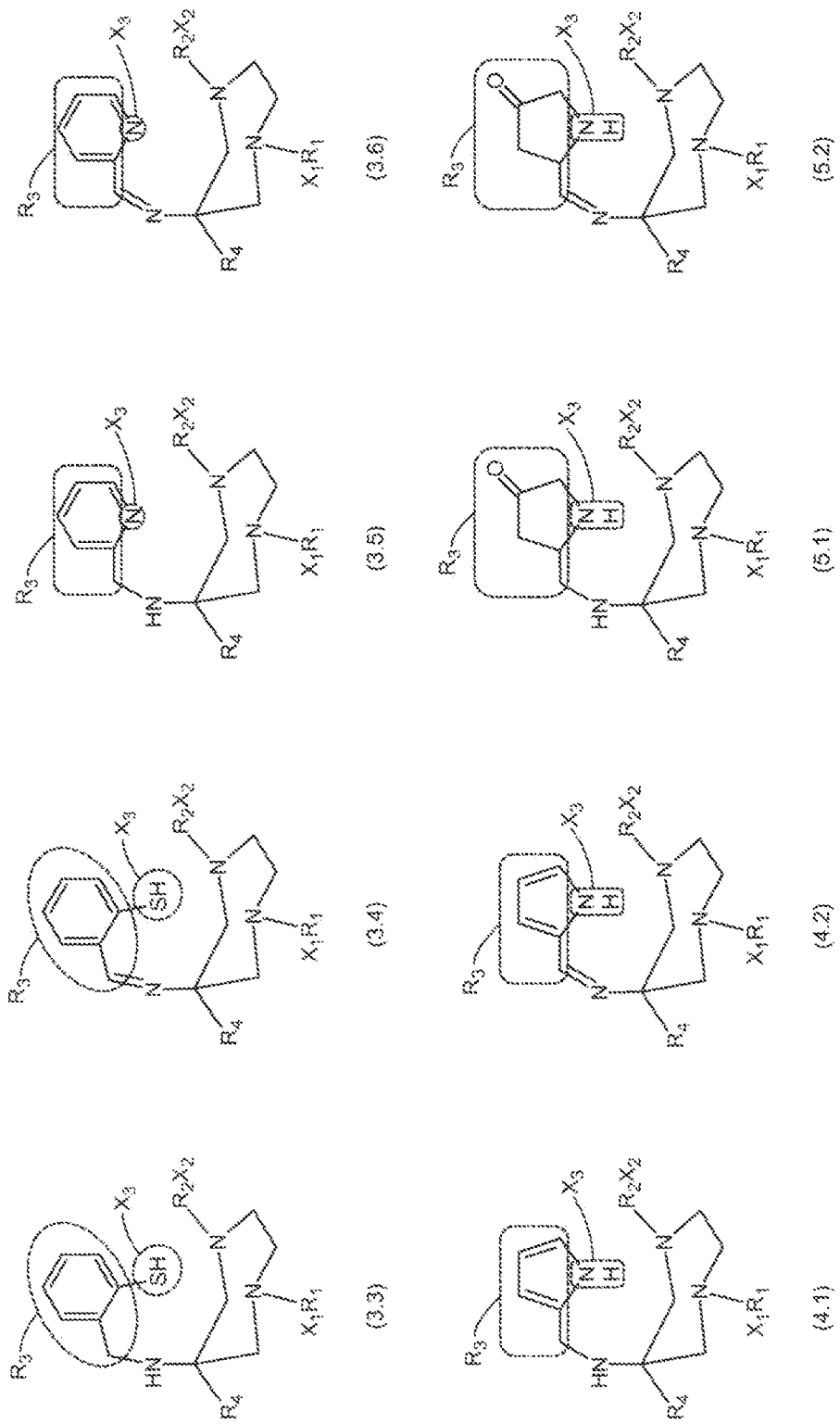
Figure 4:
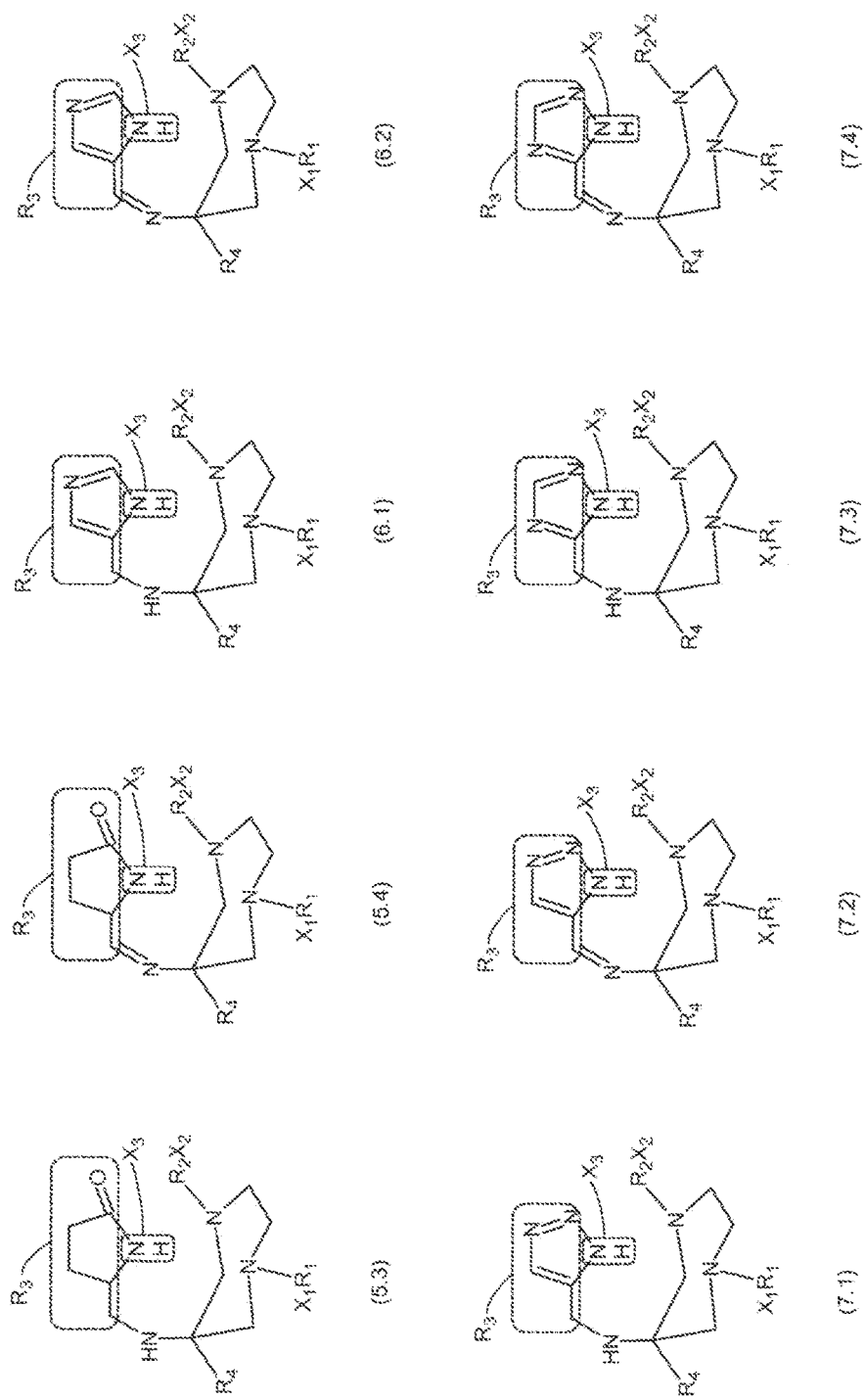
Figure 5:
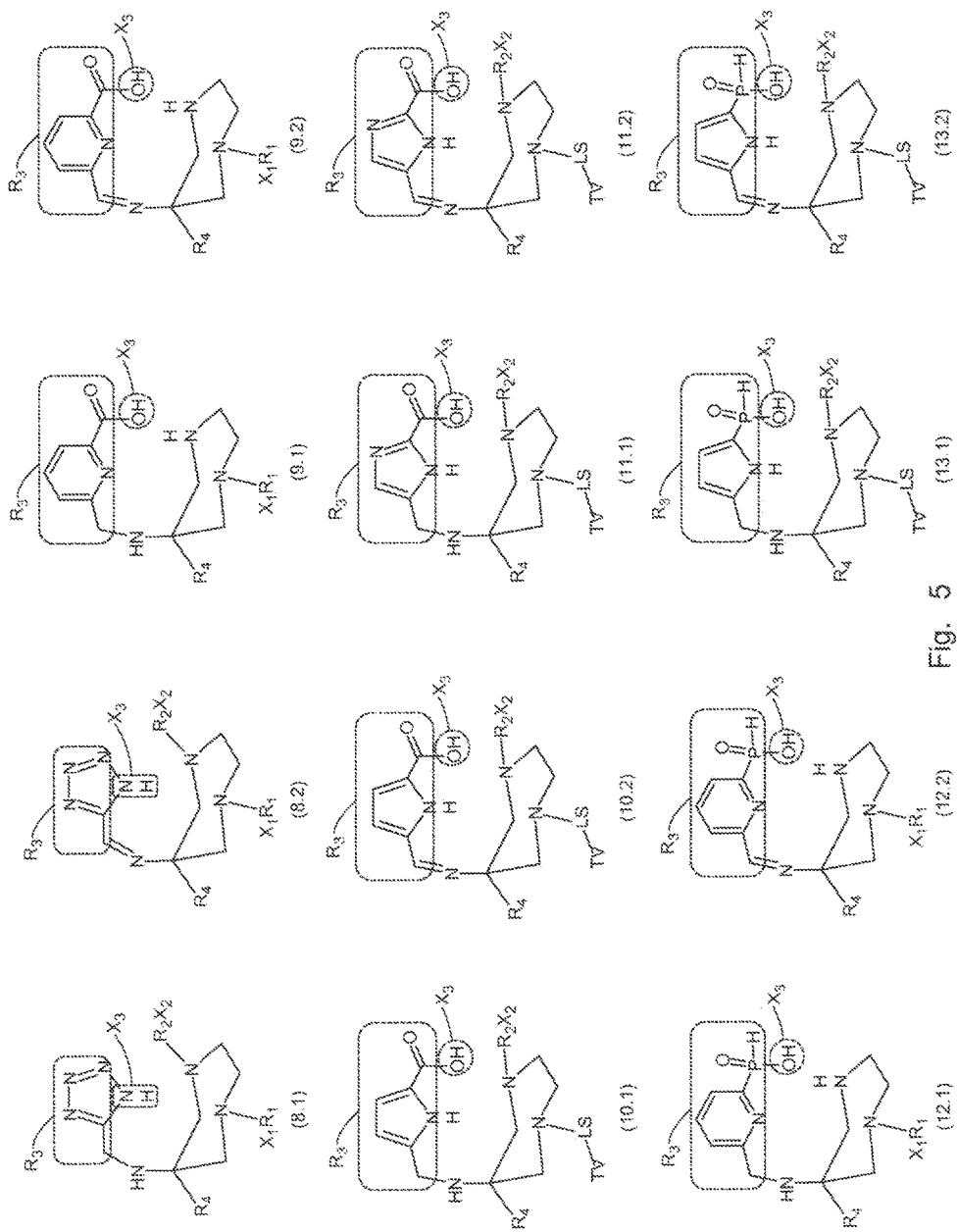

The invention pertains to a compound C for radio metal complexation comprising a chelator and one or more biological targeting vectors TV conjugated to said chelator, wherein the chelator has structure (A) or (B) or (C) based on 1,4-diazepine with groups $R_1$, $R_2$, $R_3$, $R_4$, $X_1X_2$, $X_3$;

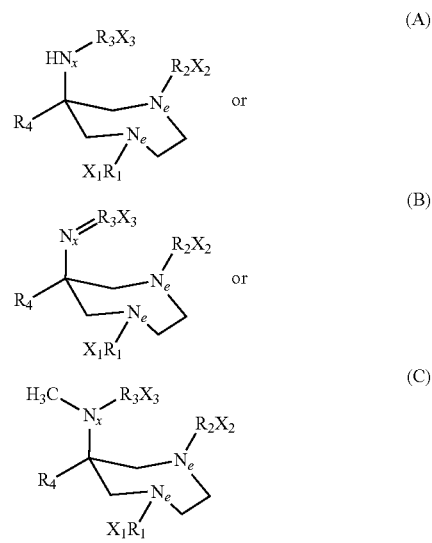

$X_1$ and $X_2$ independently of one another are vacant, OH, SH, N or NH;

$X_3$ is OH, SH, N or NH;

$R_1$, $R_2$ independently of one another are H, $CH_2$—CO, $CH_2$—POH, $CH_2$—POOH, $CH_2$—($C_6H_4$), $CH_2$—($C_5H_4$), $CH_2$—($C_{(4-m)}H_{(3-m)}N_m$), $CH_2$—($C_4H_5O$), $CH(CH_3)$—CO, $CH(CH_3)$—POH, $CH(CH_3)$—POOH, $CH(CH_3)$—($C_6H_4$), $CH(CH_3)$—($C_5H_4$), $CH(CH_3)$—($C_{(4-m)}H_{(3-m)}N_m$) or $CH(CH_3)$—($C_4H_5O$);

$R_3$ is $CH_2$—CO, $CH_2$—POH, $CH_2$—POOH, $CH_2$—($C_6H_4$), $CH_2$—($C_5H_4$), $CH_2$—($C_{(4-m)}H_{(3-m)}N_m$), $CH_2$—($C_4H_5O$), CH—CO, CH—POH, CH—POOH, CH—($C_6H_4$), CH—($C_5H_4$), CH—($C_{(4-m)}H_{(3-m)}N_m$), CH—($C_4H_5O$), $CH_2$—($C_5H_3N$)—CO, $CH_2$—($C_{(4-p)}H_{(3-p)}N_p$)—CO, CH—($C_5H_3N$)—CO, CH—($C_{(4-p)}$ $H_{(3-p)}N_p)$—CO, $CH_2$—$(C_5H_3N)$—(PH)O, $CH_2$—$(C_{(4-p)}H_{(3-p)}N_p)$—(PH)O, CH—$(C_5H_3N)$—(PH)O or CH—$(C_{(4-p)}H_{(3-p)}N_p)$—(PH)O;

$R_4$ is $CH_3$, $CH(CH_3)_2$, $C(CH_3)_3$, $(C_6H_5)$, $(C_5H_4N)$, $(C_4H_5NHO)$ or $(C_{(5-k)}H_{(5-k)}N_k)$;

wherein ($C_6H_5$) and ($C_6H_4$) designate a phenyl and phenylene ring, respectively;

($C_5H_4$) designates a cyclic residue, which is complemented by $X_1$=N, $X_2$=N, $X_3$=N, independently of one another, to give a pyridine residue;

($C_{(4-m)}H_{(3-m)}N_m$) designates a cylic residue with m=0, 1, 2 or 3; which is complemented by $X_1$=NH, $X_2$=NH, $X_3$=NH, independently of one another, to give a pyrrole, imidazole, triazole or tetrazole residue;

($C_{(5-k)}H_{(5-k)}N_k$) with k=1, 2, 3 or 4 designates a pyrrole, imidazole, triazole or tetrazole residue;

($C_4H_5O$) designates a cyclic residue, which is complemented by $X_1$=NH, $X_2$=NH, $X_3$=NH, independently of one another, to give a pyrrolidone residue;

($C_4H_5NHO$) designates a pyrrolidone residue;

($C_5H_3N$) and ($C_5H_4N$) designate pyridine residues;

($C_{(4-p)}H_{(3-p)}N_p$) with p=1, 2 or 3 designates a pyrrole, imidazole or triazole residue;

and the one or more targeting vectors TV independently of one another are conjugated at $R_1$, $R_2$, $R_3$, $R_4$, at a methyl residue at the exocyclic nitrogen atom $N_x$ and/or at the $CH_2$-residues of the 1,4-diazepine ring via optional linker/spacer groups LS, whereby one or more hydrogen atoms of $R_1$, $R_2$, $R_3$, $R_4$, of the methyl residue at the exocyclic nitrogen atom $N_x$ and/or of the $CH_2$-residues of the 1,4-diazepine ring are substituted.

In structure (A), (B) and (C) groups $X_1$, $X_2$, $X_3$ designate OH, SH, N or NH residues, which in conjunction with the two endocyclic nitrogen residues $N_e$ of the 7-membered 1,4-diazepine ring and the third exocyclic nitrogen residue $N_x$ residue ligate or bind a radio-isotopic metal. Groups $X_1$, $X_2$, $X_3$ and the two endocyclic nitrogen residues $N_e$ and the exoclyclic nitrogen residue $N_x$ provide for hexadentate ligation of the radio-isotopic metal, preferably selected from $^{66}$Ga(III), $^{67}$Ga(III) and $^{68}$Ga(III).

Advantageous embodiments of the inventive compound C are characterized in that:

the chelator has structure (B);

$R_3$ is CH—CO, CH—POH, CH—POOH, CH—$(C_6H_4)$, CH—$(C_5H_4)$, CH—$(C_{(4-m)}H_{(3-m)}N_m)$, CH—$(C_4H_5O)$, CH—$(C_5H_3N)$—CO, CH—$(C_{(4-p)}H_{(3-p)}N_p)$—CO, CH—$(C_5H_3N)$—(PH)O or CH—$(C_{(4-p)}H_{(3-p)}N_p)$—(PH)O;

$R_4$ is $CH_3$; and the one or more targeting vectors TV independently of one another are conjugated at $R_1$, $R_2$, $R_3$ and/or at the $CH_2$-residues of the 1,4-diazepine ring via optional linker/spacer groups LS, whereby one or more hydrogen atoms of $R_1$, $R_2$, $R_3$ and/or of the $CH_2$-residues of the 1,4-diazepine ring are substituted;

the chelator has structure (A) or (B) or (C);

$R_3$ is $CH_2$—CO, $CH_2$—POH, $CH_2$—POOH, $CH_2$—$(C_6H_4)$, $CH_2$—$(C_5H_4)$, $CH_2$—$(C_{(4-m)}H_{(3-m)}N_m)$, $CH_2$—$(C_4H_5O)$, CH—CO, CH—POH, CH—POOH, CH—$(C_6H_4)$, CH—$(C_5H_4)$, CH—$(C_{(4-m)}H_{(3-m)}N_m)$, CH—$(C_4H_5O)$, $CH_2$—$(C_5H_3N)$—CO, $CH_2$—$(C_{(4-p)}H_{(3-p)}N_p)$—CO, CH—$(C_5H_3N)$—CO, CH—$(C_{(4-p)}H_{(3-p)}N_p)$—CO, $CH_2$—$(C_5H_3N)$—(PH)O, $CH_2$—$(C_{(4-p)}H_{(3-p)}N_p)$—(PH)O, CH—$(C_5H_3N)$—(PH)O or CH—$(C_{(4-p)}H_{(3-p)}N_p)$—(PH)O;

$R_4$ is $CH(CH_3)_2$, $C(CH_3)_3$, $(C_6H_5)$, $(C_5H_4N)$, $(C_4H_5NHO)$ or $(C_{(5-k)}H_{(5-k)}N_k)$;

$R_1$ or $R_2$ is H;

$R_2$ or $R_1$, respectively, is $CH_2$—CO, $CH_2$—POH, $CH_2$—POOH, $CH_2$—$(C_6H_4)$, $CH_2$—$(C_5H_4)$, $CH_2$—$(C_{(4-m)}H_{(3-m)}N_m)$, $CH_2$—$(C_4H_5O)$, $CH(CH_3)$—CO, $CH(CH_3)$—POH, $CH(CH_3)$—POOH, $CH(CH_3)$—$(C_6H_4)$, $CH(CH_3)$—$(C_5H_4)$, $CH(CH_3)$—$(C_{(4-m)}H_{(3-m)}N_m)$ or $CH(CH_3)$—$(C_4H_5O)$;

$R_3$ is $CH_2$—$(C_5H_3N)$—CO, $CH_2$—$(C_{(4-p)}H_{(3-p)}N_p)$—CO, CH—$(C_5H_3N)$—CO, CH—$(C_{(4-p)}H_{(3-p)}N_p)$—CO, $CH_2$—$(C_5H_3N)$—(PH)O, $CH_2$—$(C_{(4-p)}H_{(3-p)}N_p)$—(PH)O, CH—$(C_5H_3N)$—(PH)O or CH—$(C_{(4-p)}H_{(3-p)}N_p)$—(PH)O; and $X_3$ is OH;

the steric bulk value (A-value) of $R_4$ is greater/equal 7.2 kJ/mol, greater/equal 8.8 kJ/mol or greater/equal 12.6 kJ/mol;

the number of atomic bonds along the shortest path between the exocyclic nitrogen $N_x$ and the N-, O- or S-atom of group $X_3$ is 3, 4 or 6;

the one or more targeting vectors TV independently of one another are selected from the group comprising amino acid residues; residues of amino acid derivatives, such as L-tyrosine, L-serine, L-lysine and Alpha-methyl-L-tyrosine; residues of peptides, such as bombesins and melanocortins; residues of Octreotide; residues of proteins; residues of micro proteins; antibodies, such as huKS (humanized antibody for EpCAM respectively KSA) and hu14.18 (humanized antibody for disialoganglioside GD2); recombinant antibodies; antibody fragments; bisphosphonates; sugars; glucose; fructose; sucrose; glutamine; glucosamine; lipids; nucleotides; nucleosides; DNA-components; hypoxia tracers, such as 2-nitroimidazole; azomycine (2-nitroimidazole-arabinoside); erythronitroimidazole; ethyltyrosine; 2-(2-nitro-(1)H-imidazole-1-yl)-N-(2,2,3,3,3-pentafluoropropyl)-acetamide (EF5); liposomes; polymers and nanoparticles;

the one or more targeting vectors TV independently of one another are conjugated at $R_1$, $R_2$, $R_3$ or $R_4$ via optional linker/spacer groups LS;

one or more targeting vectors TV are conjugated at $R_4$ via optional linker/spacer groups LS; and/or the linker/spacer groups LS independently of one another are residues of molecules selected from the group comprising linear, branched or hetero substituted, saturated and unsaturated aromatic hydrocarbons of all oxidation states; linear, branched or hetero substituted alkyls, alkylenes, alkylidenes, aryls, polyethers, polypeptides or sugars.

Inventors, based on extensive experimentation, have surprisingly found, that compounds according to the above specified structures (A), (B) and (C) afford highly efficient, fast and stable complexation of metals, such as Ga(III). The reasons for the favorable complexation efficacy of the inventive compound C are not yet fully understood. It is believed, that the inventive combination of groups $R_1$, $R_2$, $R_3$, $R_4$ fulfill stereochemical conditions which promote complexation of metals, such as Ga(III). In particular, the inventive compounds seem to share the feature that the steric bulk (or so called A-value) of $R_4$ is appreciably larger than that of the exocylic nitrogen $N_x$. Furthermore, it appears important to select groups $R_1$, $R_2$, $R_3$ in such manner, that their total steric bulk, i.e. the sum of the A-values of $R_1$, $R_2$, $R_3$ does not exceed a certain limit. In addition, inventors have found that there exists an upper limit for the sum of the A-values of $R_4$ and $N_x$ which is enforced by predominantly steric restrictions. From the experiments conducted by the inventors it is concluded, that $R_4$ and $N_x$ must be chosen in such manner, that the sum of the A-values of $R_4$ and $N_x$ is less than 26 kJ mol, less than 25 kJ mol, less than 24 kJ/mol, less than 23 kJ/mol, less than 22 kJ/mol, less than 21 kJ/mol, less than 20 kJ/mol, less than 19 kJ/mol, less than 18 kJ/mol, less than 17 kJ/mol, less than 16 kJ/mol, less than 15 kJ/mol, less than 14 kJ/mol, less than 13 kJ/mol, less than 12 kJ/mol or less than 11 kJ/mol.

Furthermore, $R_4$ and $N_x$ are preferably chosen in such manner that the ratio of the A-value of $R_4$ over the A-value of $N_x$ is greater than 8:1, greater than 7:1, greater than 6:1, greater than 5:1, greater than 4:1, greater than 3:1, greater than 2:1 or greater than 1.6:1.

The A-values recited in this invention for $R_1$, $R_2$, $R_3$, and $N_x$ refer to energy measurements of a monosubstituted cyclohexane ring according to "Glossary of terms used in physical organic chemistry (IUPAC Recommendations 1994)"; P. Müller, PAC 66 (5): 1077-1184. Exemplary A-values are presented in Table 1.

TABLE 1

| Substituent | A-Value [kJ/mol] | Substituent | A-Value [kJ/mol] | Substituent | A-Value [kJ/mol] |
|---|---|---|---|---|---|
| D | 0.03 | $CH_2Br$ | 7.49 | $OSi(CH_3)_3$ | 3.10 |
| F | 0.63 | $CH(CH_3)_2$ | 9.00 | OH | 3.64 |
| Cl | 1.80 | $c-C_6H_{11}$ | 9.00 | $OCH_3$ | 2.51 |
| Br | 1.59 | $C(CH_3)_3$ | >16.74 | $OCD_3$ | 2.34 |
| I | 1.80 | Ph | 12.55 | $OCH_2CH_3$ | 3.77 |
| CN | 0.71 | $C_2H$ | 5.65 | O-Ac | 2.51 |
| NC | 0.88 | $CO_2^-$ | 8.03 | O-TFA | 2.85 |
| NCO | 2.13 | $CO_2CH_3$ | 5.31 | OCHO | 1.13 |
| NCS | 1.17 | $CO_2Et$ | 5.02 | O-Ts | 2.09 |
| N=C=NR | 4.18 | $CO^iPr$ | 4.02 | $ONO_2$ | 2.47 |
| $CH_3$ | 7.11 | COCl | 5.23 | $NH_2$ | 6.69 |
| $CF_3$ | 8.79 | $COCH_3$ | 4.90 | $NHCH_3$ | 4.18 |
| $CH_2CH_3$ | 7.32 | SH | 3.77 | $N(CH_3)_3$ | 8.79 |
| $CH=CH_2$ | 5.65 | SMe | 2.93 | $NH_3^+$ | 7.95 |
| CCH | 1.72 | SPh | 3.35 | $NO_2$ | 4.60 |
| $CH_2^tBu$ | 8.37 | $S^-$ | 5.44 | HgBr | ~0.00 |
| $CH_2OTs$ | 7.32 | SOPh | 7.95 | HgCl | 1.26 |
|  |  | $SO_2Ph$ | 10.46 | $Si(CH_3)_3$ | 10.46 |

Substituents on a cyclohexane ring prefer to reside in the equatorial position rather than the axial position. Thus, in the case when there is more than one substituent present, the substituent with the largest A-value is more likely to take up the less hindered equatorial orientation whilst the other is predisposed to an axial orientation. The A-value of a particular substituent is defined as the difference in Gibbs free energy ($\Delta G$) between the higher energy conformation (axial substitution) and the lower energy conformation (equatorial substitution) of the substituent conjugated to cyclohexane and can be determined from reaction equilibrium constants.

Inventors further found it advantageous, to conjugate the one or more targeting vectors TV at $R_1$, $R_2$, $R_3$ or $R_4$, rather than at the four $CH_2$-residues of the 1,4-diazepine ring and/or the exocyclic nitrogen $N_x$ directly, thus reducing total steric bulk proximal the three endo- and exocyclic nitrogen residues $N_e$, $N_e$ and $N_x$. Large steric bulk proximal to the nitrogen residues $N_e$, $N_e$ and $N_x$ adversely affects the complexation efficacy of the chelating moiety.

Inventors further found it advantageous, to conjugate the one or more targeting vectors TV at $R_4$, rather than at $R_1$, $R_2$, $R_3$, thus minimizing interference with the ligating function of groups $R_1X_1$, $R_2X_2$ and $R_3X_3$.

The invention further pertains to a method for preparation of radiolabeled biological markers comprising the steps of
(a) providing a solution S containing the compound C as specified above;
(b) providing a radioactive metal R, such as $^{68}$Ga(III), adsorbed on a ion exchanger; and
(c) ligating the radioactive metal R with the compound C to form a complex RC of the radioactive metal R and the compound C in a solution F.

Advantageous embodiments of the inventive method are characterized in that:
in step (c) the radioactive metal R is eluted from the ion exchanger using the solution S;
in step (c) the radioactive metal R is eluted from the ion exchanger with a solvent E to obtain a solution RE, containing the radioactive metal R, and the solution RE is admixed with the solution S to obtain the solution F with the complex RC;
in step (c) prior to elution of the radioactive metal R, the ion exchanger is purged with one or more solvents to remove impurities;
the ion exchanger is a cation exchanger;
the ion exchanger comprises sulfonated poly(styrene-co-divinylbenzene) resin as active component, wherein the poly(styrene-co-divinylbenzene) resin contains divinylbenzene in an amount of 2 to 20 mol-% based on 100 mol-% of styrene and divinylbenzene monomer units;
subsequent to step (c) the solution F is filtered and/or neutralized;
step (c) is completed within 6 s to 5 min, within 6 s to 3 min, within 6 s to 2 min or preferably within 6 s to 1 min;
step (c) is conducted at a temperature from 10 to 60° C., from 10 to 40° C. or preferably from 10 to 30° C.; and/or
in step (b) a radionuclide generator is employed, wherein the radionuclide generator comprises a parent radionuclide, such as $^{68}$Ge, and a daughter radionuclide, such as $^{68}$Ga, which are adsorbed on a chromatographic column, and the daughter radionuclide is eluted from the chromatographic column prior to adsorption onto the ion exchanger.

The invention is further described with reference to FIG. 1-10, wherein

Figure 6:
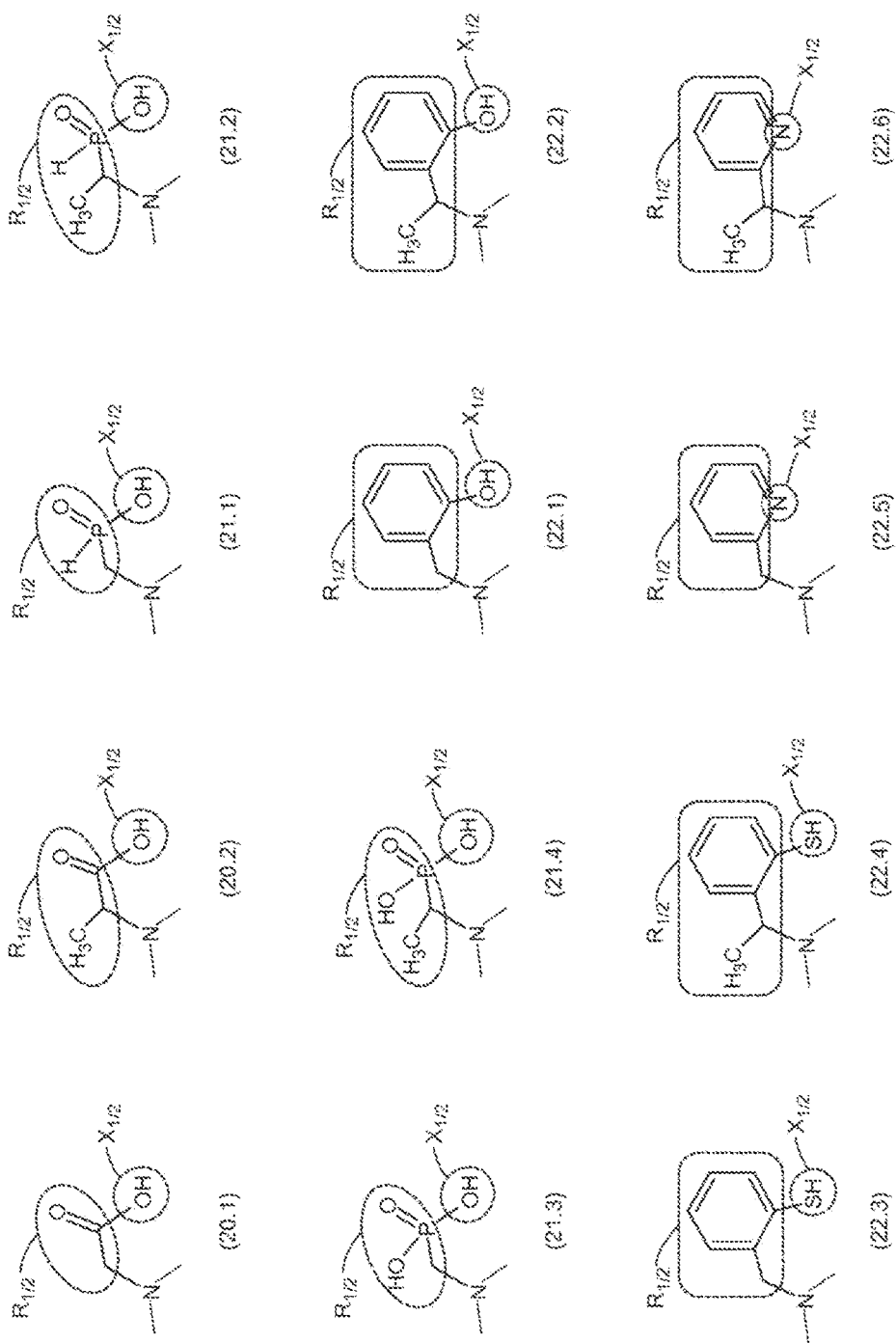
FIGS. 6 through 8 show sections of embodiments of the chelator of the inventive compound C according to structures (20.1) to (20.2), (21.1) to (21.4), (22.1) to (22.6), (23.1) to (23.2), (24.1) to (24.4), (25.1) to (25.2), (26.1) to (26.4), (27.1) to (27.2) with various groups R1, X1 and R2, X2.
Figure 7:
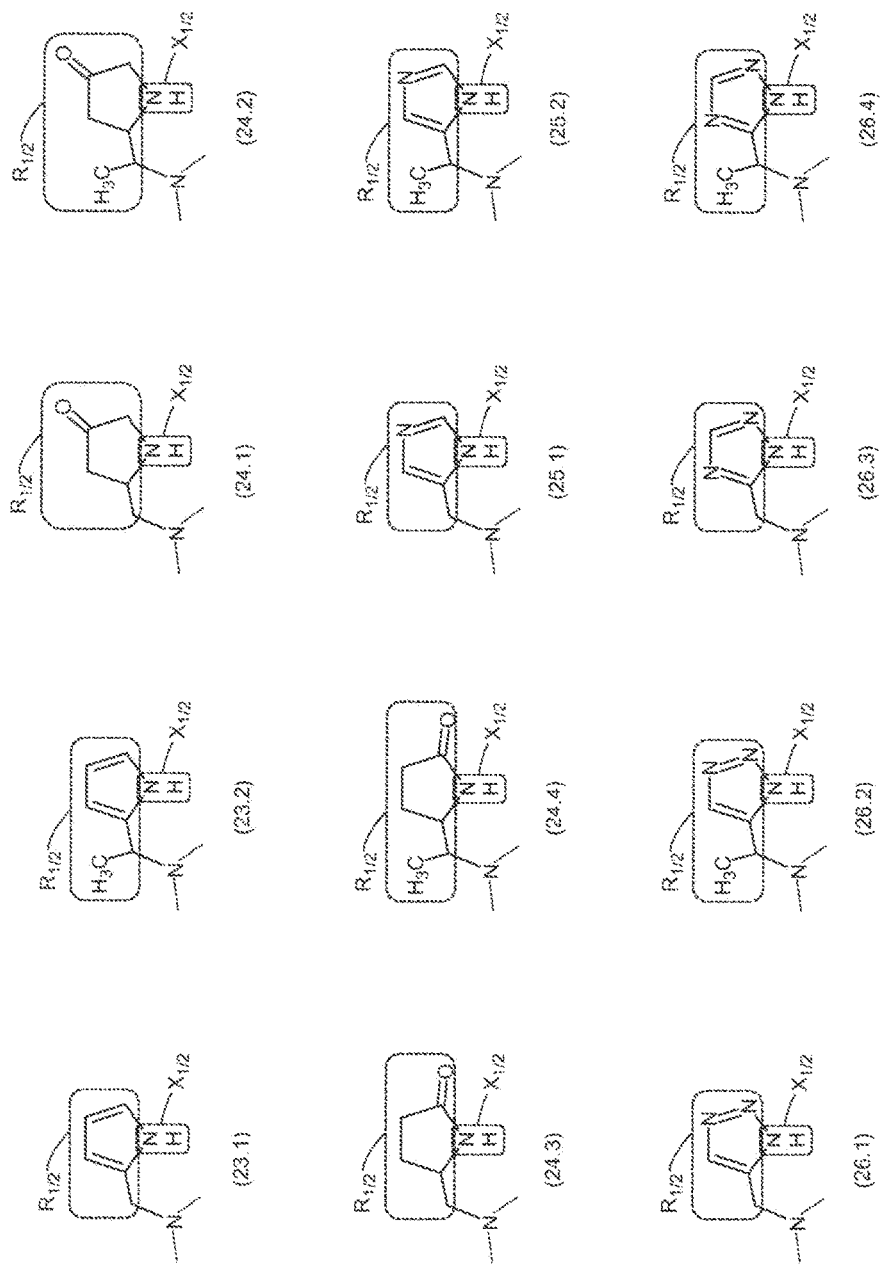
Figure 8:
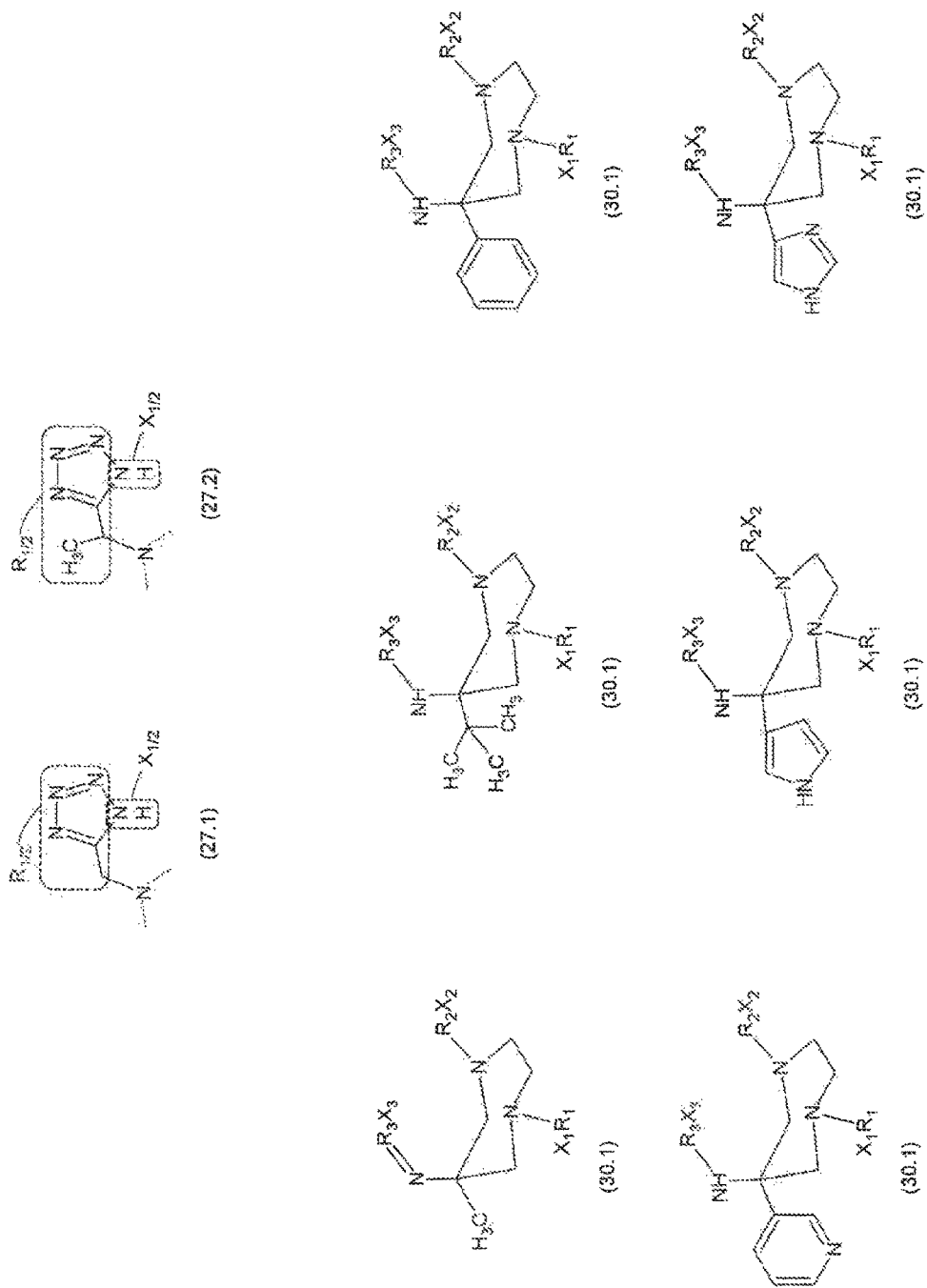
Figure 9:
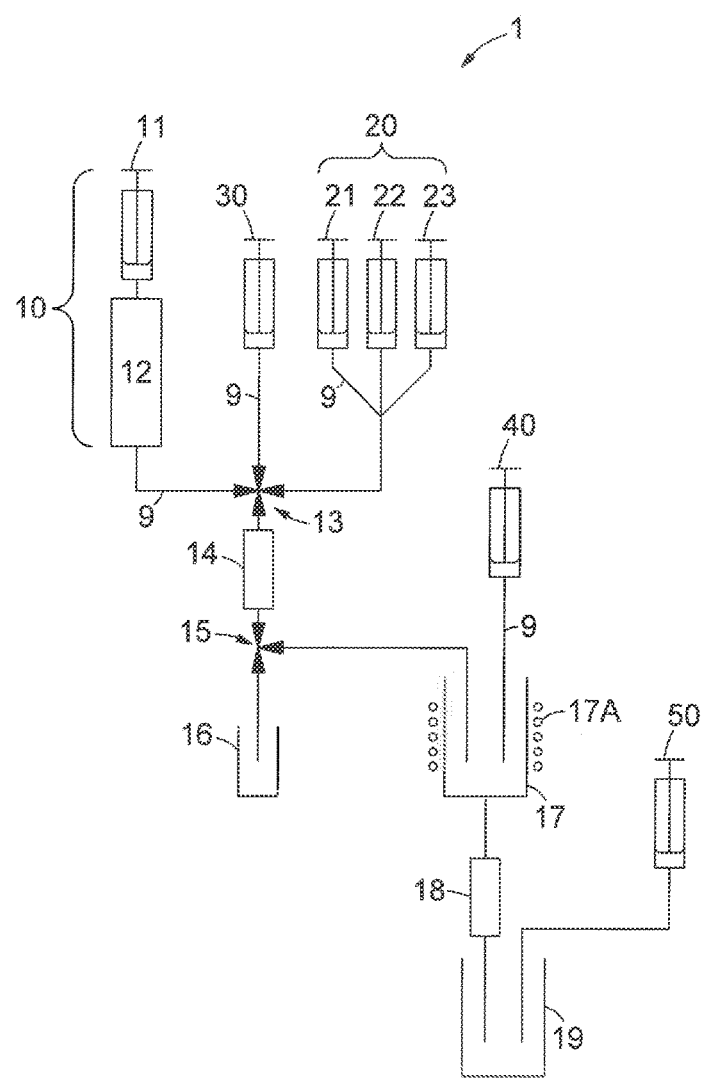
FIGS. 9 and 10 schematically show a first and second apparatus, respectively, for preparing a radio-labelled complex consisting of the inventive compound C and a therewith ligated radio-isotopic metal.
Figure 10:
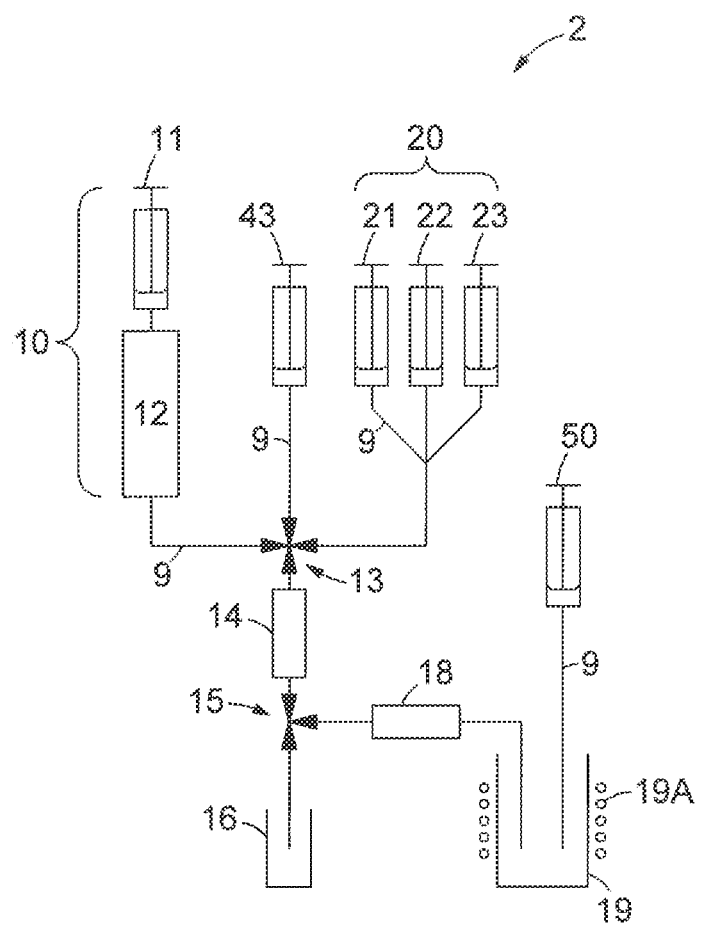

FIG. 1 shows embodiments of the inventive compound C according to general structures (A.1) to (A.4), (B.1) to (B.4) and (C.1) to (C.4) with a targeting vector TV attached at either of groups $R_1$, $R_2$, $R_3$, $R_4$ or at the methyl residue at the exocyclic nitrogen atom $N_x$;

FIG. 2-5 show embodiments of the chelator of the inventive compound C according to structures (1.1) to (1.2), (2.1) to (2.4), (3.1) to (3.6), (4.1) to (4.2), (5.1) to (5.4), (6.1) to (6.2), (7.1) to (7.4), (8.1) to (8.2), (9.1) to (9.2), (10.1) to (10.2) and (11.1) to (11.2) with various groups $R_3$ and $X_3$;

FIG. 6-8 show sections of embodiments of the chelator of the inventive compound C according to structures (20.1) to (20.2), (21.1) to (21.4), (22.1) to (22.6), (23.1) to (23.2), (24.1) to (24.4), (25.1) to (25.2), (26.1) to (26.4), (27.1) to (27.2) with various groups $R_1$, $X_1$ and $R_2$, $X_2$; and FIG. 9-10 schematically show a first and second apparatus, respectively, for preparing a radio-labelled complex consisting of the inventive compound C and a therewith ligated radio-isotopic metal.

As indicated in FIG. 1, according to structures (A.1) to (A.4) and (B.1) to (B.4), targeting vectors TV are conjugated to the chelator via optional linker/spacer groups LS at either of groups $R_1$, $R_2$, $R_3$ and/or $R_4$.

The invention further encompasses compounds C, wherein two or more targeting vectors TV, which are equal or different are conjugated at two or more of groups $R_1$, $R_2$, $R_3$, $R_4$ and/or the $CH_2$-residues of the 1,4-diazepine via optionally two or more linker/spacer groups LS, which are equal or different.

FIG. 2-5 show various embodiments of ligating group $R_3X_3$. The chemical structure of $R_3X_3$, or the basic group, of which $R_3X_3$ constitutes a residue, are recited in Table 2:

TABLE 2

| Structure | $[R_3]X_3$ or $[R_3X_3]$ basic group |
|---|---|
| (1.1), (1.2) | [$CH_2$/CH—CO]OH |
| (2.1), (2.2) | [$CH_2$/CH—PHO]OH |
| (2.3), (2.4) | [$CH_2$/CH—$PHO_2$]OH |
| (3.1), (3.2), (3.3), (3.4) | [$CH_2$/CH-phenylene]OH/SH |
| (3.5), (3.6) | [$CH_2$/CH-pyridine] |
| (4.1), (4.2) | [$CH_2$/CH-pyrrole] |
| (5.1), (5.2), (5.3), (5.4) | [$CH_2$/CH-pyrrolidone] |
| (6.1), (6.2) | [$CH_2$/CH-imidazole] |
| (7.1), (7.2), (7.3), (7.4) | [$CH_2$/CH-triazole] |
| (8.1), (8.2) | [$CH_2$/CH-tetrazole] |
| (9.1), (9.2) | [$CH_2$/CH-pyridine-CO]OH |
| (10.1), (10.2) | [$CH_2$/CH-pyrrole-CO]OH |
| (11.1), (11.2) | [$CH_2$/CH-imidazole-CO]OH |
| (12.1), (12.2) | [$CH_2$/CH-pyridine-(PH)O]OH |
| (13.1), (13.2) | [$CH_2$/CH-pyrrole-(PH)O]OH |

In Table 2, the term "$CH_2$/CH" designates either $CH_2$ or CH and the term "OH/SH" refers to either OH or SH.

Structures (9.1), (9.2), (10.1), (10.2), (11.1), (11.2), (12.1), (12.2), (13.1), (13.2) pertain to specific embodiments, wherein $R_3X_3$ provides bidentate ligating function and one of $R_1X_1$ and $R_2X_2$ is substituted by hydrogen or employed as attachment site for a targeting vector TV, optionally conjugated via linker/spacer group LS.

FIG. 6-8 show various embodiments of ligating groups $R_1X_1$ and $R_2X_2$. The chemical structure of $R_1X_1$ and $R_1X_1$, or the basic group, of which $R_1X_1$ and $R_2X_2$ constitute a residue, are recited in Table 3:

TABLE 3

| Structure | $[R_{1/2}]X_{1/2}$ or $[R_{1/2}X_{1/2}]$ basic group |
|---|---|
| (20.1), (20.2) | [$CH_2$/$CH_3$—CO]OH |
| (21.1), (21.2) | [$CH_2$/$CH_3$—PHO]OH |
| (21.3), (21.4) | [$CH_2$/$CH_3$—$PHO_2$]OH |
| (22.1), (22.2), (22.3), (22.4) | [$CH_2$/$CH_3$-phenylene]OH/SH |
| (22.5), (22.6) | [$CH_2$/$CH_3$-pyridine] |
| (23.1), (23.2) | [$CH_2$/$CH_3$-pyrrole] |
| (24.1), (24.2), (24.3), (24.4) | [$CH_2$/$CH_3$-pyrrolidone] |
| (25.1), (25.2) | [$CH_2$/$CH_3$-imidazole] |
| (26.1), (26.2), (26.3), (26.4) | [$CH_2$/$CH_3$-triazole] |
| (27.1), (27.2) | [$CH_2$/$CH_3$-tetrazole] |

Groups $R_1X_1$ and $R_2X_2$ are selected independently of one another from the structures, recited in Table 3, FIG. 6-8 or in the claims. In Table 3, the term "$CH_2$/$CH_3$" designates either $CH_3$ or $CH_3$ and the term "OH/SH" refers to either OH or SH.

FIG. 9 schematically shows a first apparatus 1 for preparation of a complex consisting of the inventive compound C and a radio-isotopic metal, preferably selected from $^{66}Ga$, $^{67}Ga$ and $^{68}Ga$. Apparatus 1 comprises a radionuclide generator 10 with a chromatographic column 12, whereon a radiometallic parent nuclide, such as $^{68}Ge$, and its corresponding daughter nuclide R are adsorbed, and an eluant supply device 11 for elution of daughter nuclide R from chromatographic column 12 with a suitable solvent. The various components of apparatus 1 are connected via fluid conduits, which in FIG. 9 are collectively designated by reference sign 9. The exit or outlet of chromatographic column 12 is connected via a fluid conduit and a first multiport valve 13 to the inlet of a ion exchanger 14. The ion exchanger 14 preferably comprises sulfonated poly(styrene-co-divinylbenzene) resin as active component, wherein the poly(styrene-co-divinylbenzene) resin contains divinylbenzene in an amount of 2 to 20 mol-% based on 100 mol-% of styrene and divinylbenzene monomer units. The daughter nuclide R eluted from chromatographic column 12 is adsorbed onto ion exchanger 14 and concomitantly eluted parent nuclide is practically completely passed into a waste vessel 16 via a second multiport valve 15.

Apparatus 1 preferably comprises further eluant supply devices 21, 22, 23, which are connected to the inlet of ion exchanger 14 via fluid conduits and the first multiport valve 13. Supply devices 21, 22, 23 are employed to purge ion exchanger 14, i.e. the thereon adsorbed daughter nuclide R from impurities, such as residual parent nuclide, $Fe^{III}$, $Zn^{II}$ and $Ti^{IV}$, originating from the radionuclide generator 10. The one or more purging eluates respectively solvents exiting the ion exchanger 14 are also passed into waste vessel 16 via the second multiport valve 15.

A further eluant supply device 30, connected to the inlet of ion exchanger 14 via a fluid conduit and the first multiport valve 13, is employed for elution of the purified daughter nuclide R from the ion exchanger 14 via the second multiport valve 15 into a process vessel 17. Process vessel 17 is preferably equipped with an electric heater 17A. A supply device 40 is used to feed a solution, which contains the inventive compound C, into process vessel 17 and thereby initiate complexation of the daughter nuclide R with the compound C. Upon completion of the complexation reaction the solution, containing the radiolabelled compound C, i.e. the complex comprising compound C and the thereto ligated daughter nuclide R, is passed through an optional filter 18 into a product vessel 19, where it may be optionally neutralized with a solution, that is provided from a supply device 50.

FIG. 10 shows a second apparatus 2 for preparation of a complex consisting of the inventive compound C and a radio-isotopic metal, preferably selected from $^{66}Ga$, $^{67}Ga$ and $^{68}Ga$. In FIG. 10, reference signs equal to those of FIG. 9 designate components providing the same functionality. The second apparatus 2 differs from apparatus 1 in that a solution, containing the inventive compound C is fed from an eluant supply device 43 in order to elute the daughter nuclide R from ion exchanger 14 via multiport valve 15 and an optional filter 18 into product vessel 19. The high complexation efficacy of the inventive compound C and the stability of the corresponding complex formed by ligation with radio-isotopic metals, such as $^{68}Ga$, afford a simplified process wherein elution and complexation of daughter nuclide R are carried out fully or partially simultaneously.

EXAMPLE 1

Compounds of the general formula

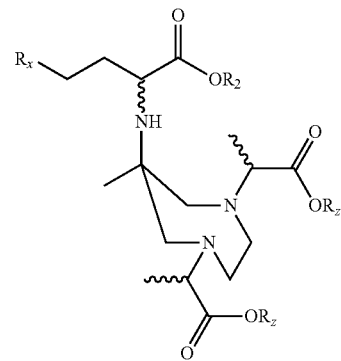

$R_x$ = Linker group
$R_z$ = protection group (Me, Et)

such as
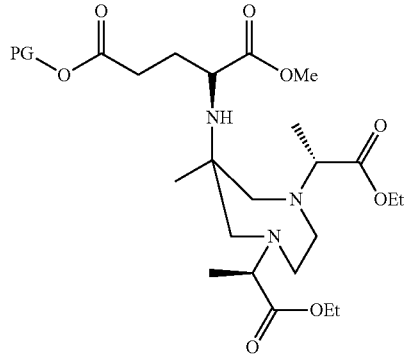
1
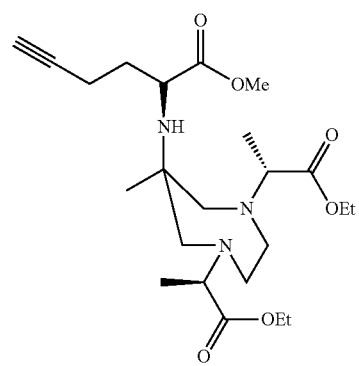
2
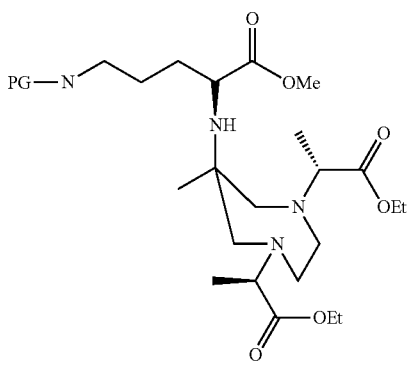
3
-continued
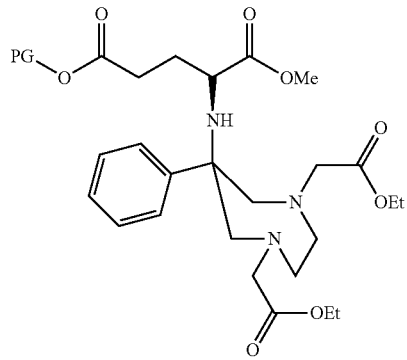
4
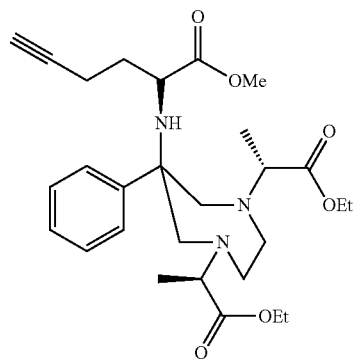
5
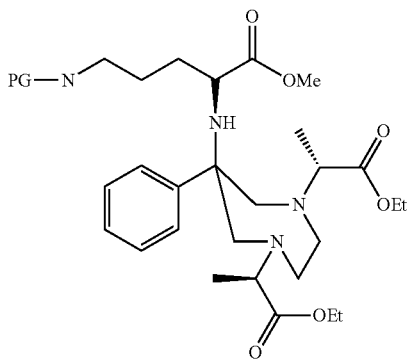
6
PG = protecting group
Optionally deprotected, complexed with a gallium isotope and/or attached to a targeting vector.
EXAMPLE 2
A method for the synthesis of a compound in EXAMPLE 1
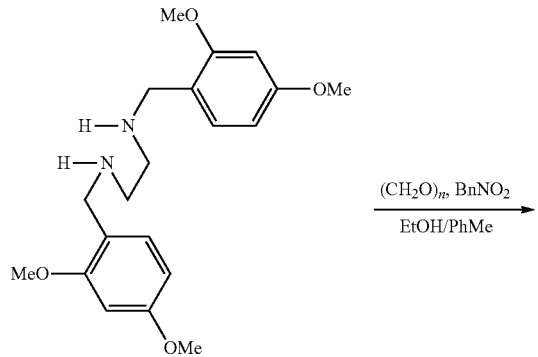

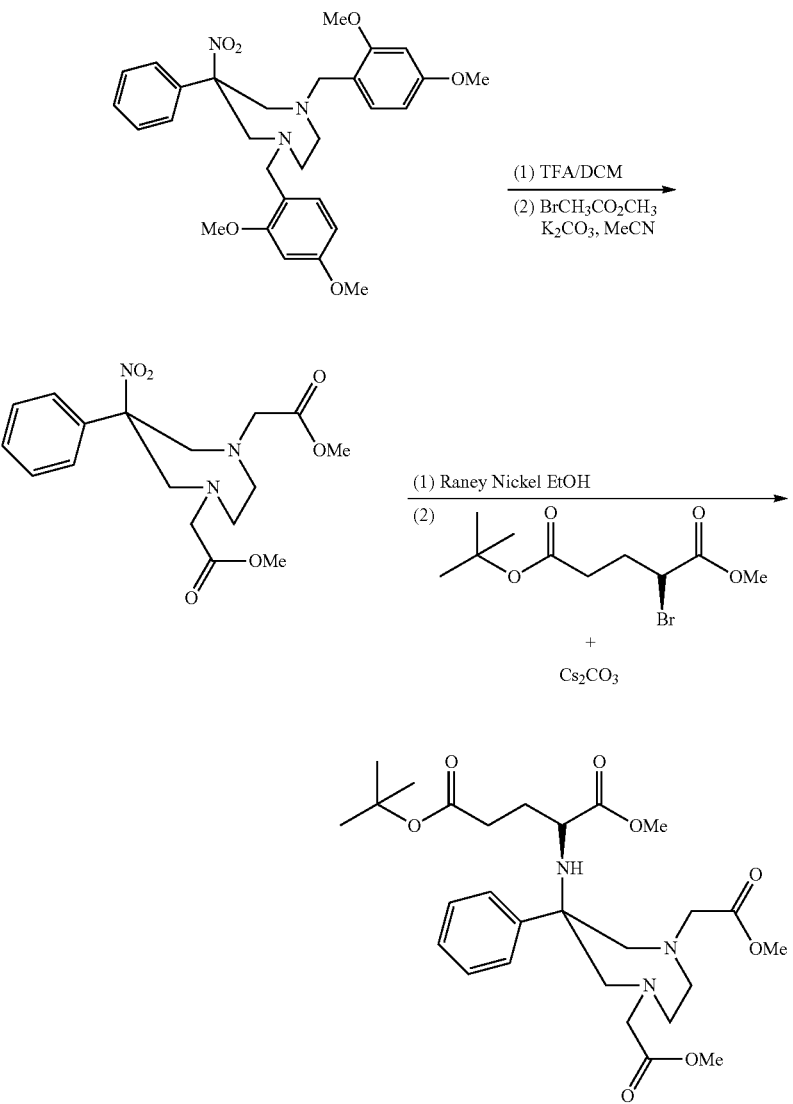
EXAMPLE 3
Compounds of the general formula
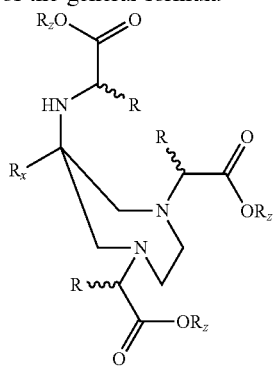
$R_x$ = Linker group
$R_z$ = protecting group (Me, Et)
R = alkyl or H
such as
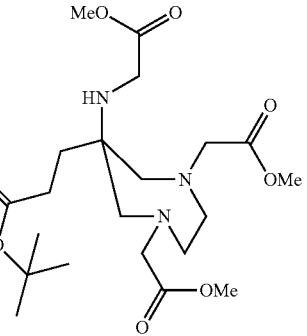

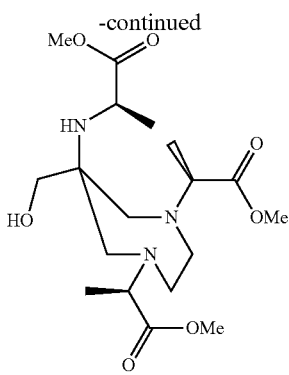
Optionally deprotected, complexed with a gallium isotope and/or attached to a targeting vector.
EXAMPLE 4
A method for the synthesis of compounds in Example 3
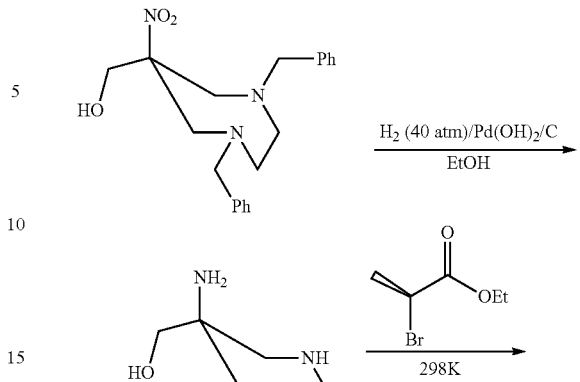
or alternatively
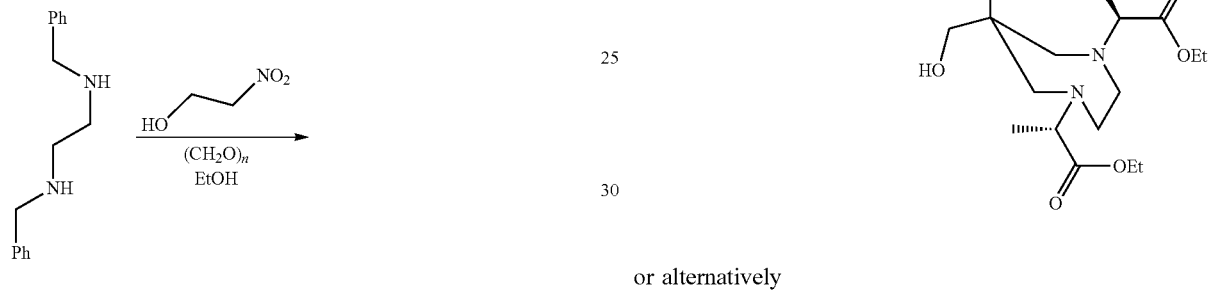
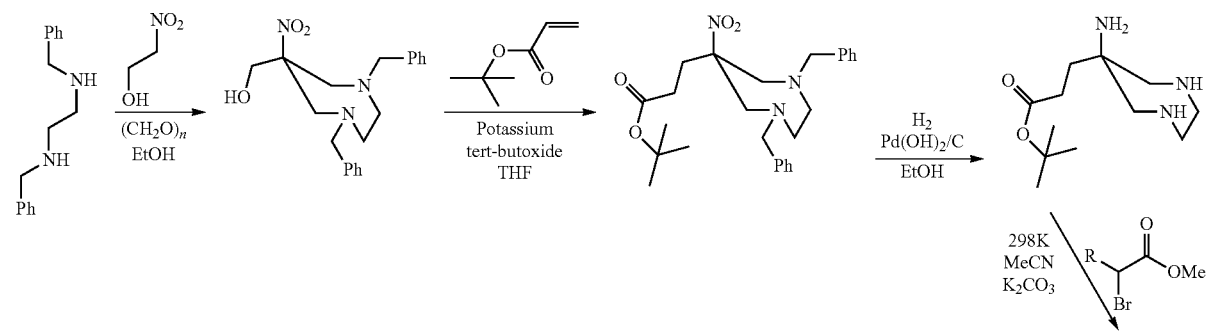
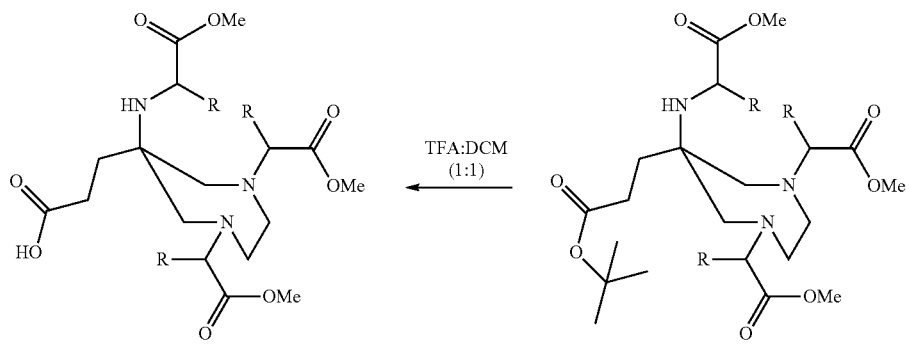
R = Me or H [best with R = Me]
ready for coupling to a TV followed by ester hydrolysis to give the free ligand (OMe converted to OH)

Leads to structures like:
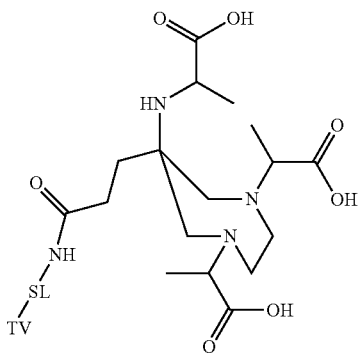
EXAMPLE 5
Compounds of the general formula
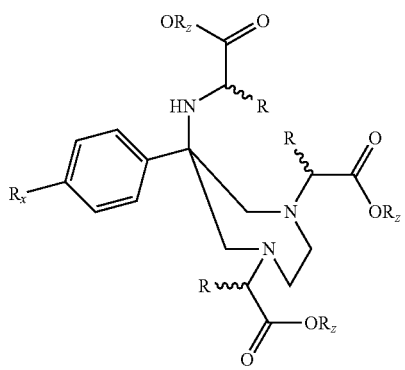
$R_x$ = Linker group
$R_z$ = protecting group (Me, Et)
R = alkyl or H
For example:
(A.1)
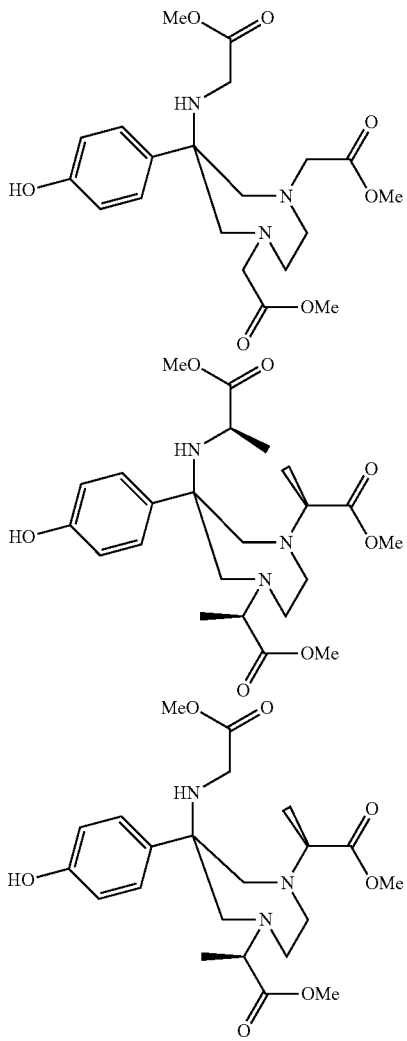
Optionally deprotected, complexed with a gallium isotope and/or attached to a targeting vector.
EXAMPLE 6
A method for the synthesis of compounds in Example 5
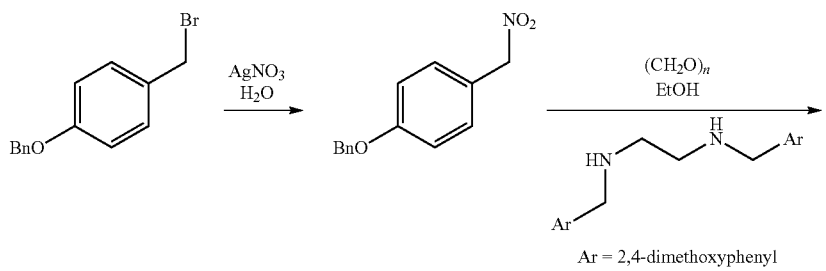
Ar = 2,4-dimethoxyphenyl -continued
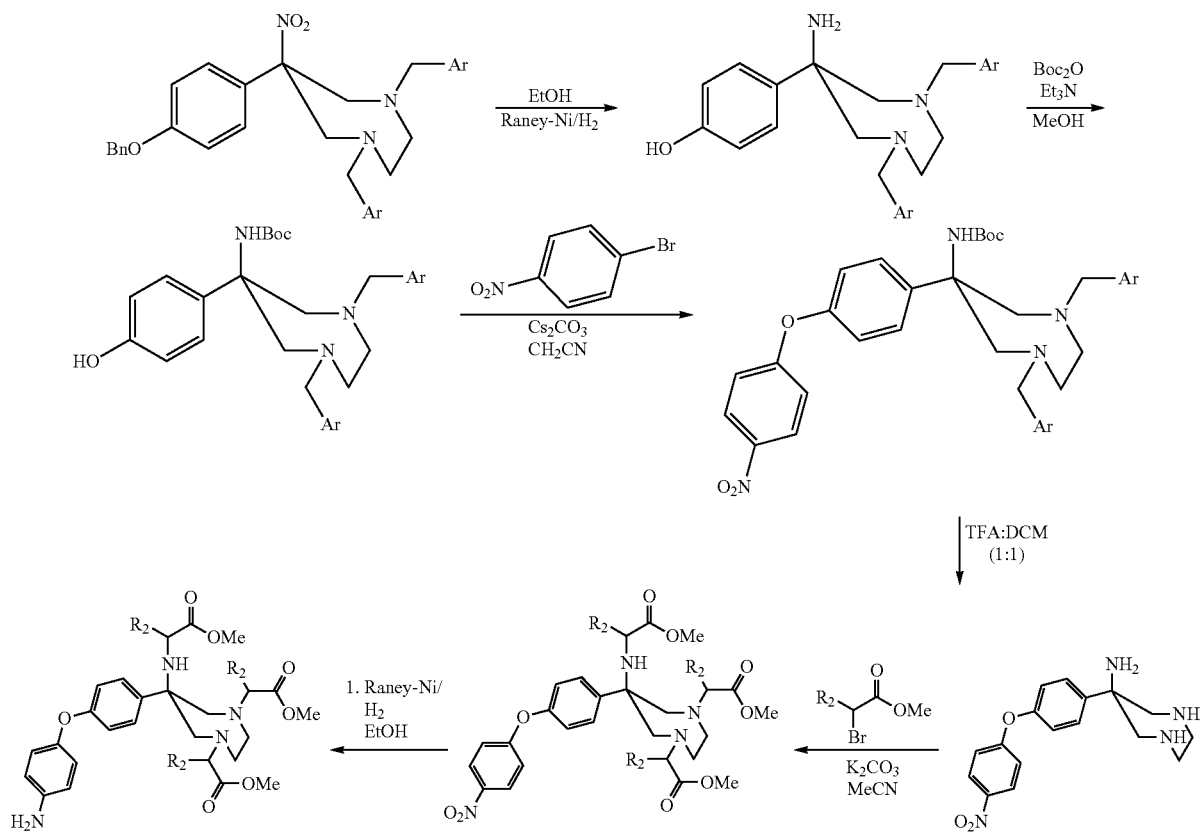
BW4a: $R_1$ = Me, $R_2$ = Me
BW4b: $R_1$ = Ph, $R_2$ = H
BW4c: $R_1$ = Ph, $R_2$ = Me
Ready for coupling with a TV
Followed by ester hydrolysis (OMe converted to Me)
Leads to A.1 type structures
EXAMPLE 7
Compounds of the general formula
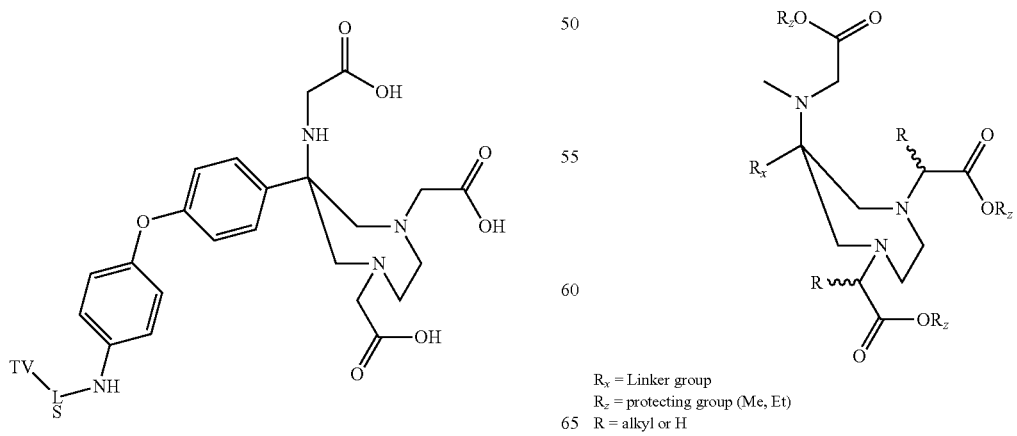
$R_x$ = Linker group
$R_z$ = protecting group (Me, Et)
R = alkyl or H such as

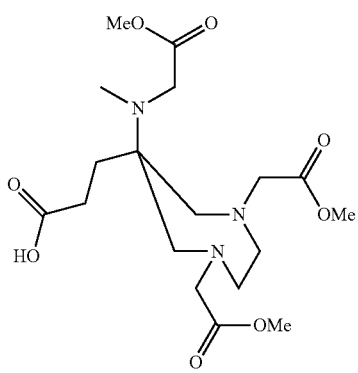 [SMILES: COC(=O)CN1CCN(CC(=O)OC)CC(CCC(=O)O)(N(C)CC(=O)OC)C1]

Optionally deprotected, complexed with a gallium isotope and/or attached to a targeting vector.

EXAMPLE 8

A method for the synthesis of compounds in Example 7

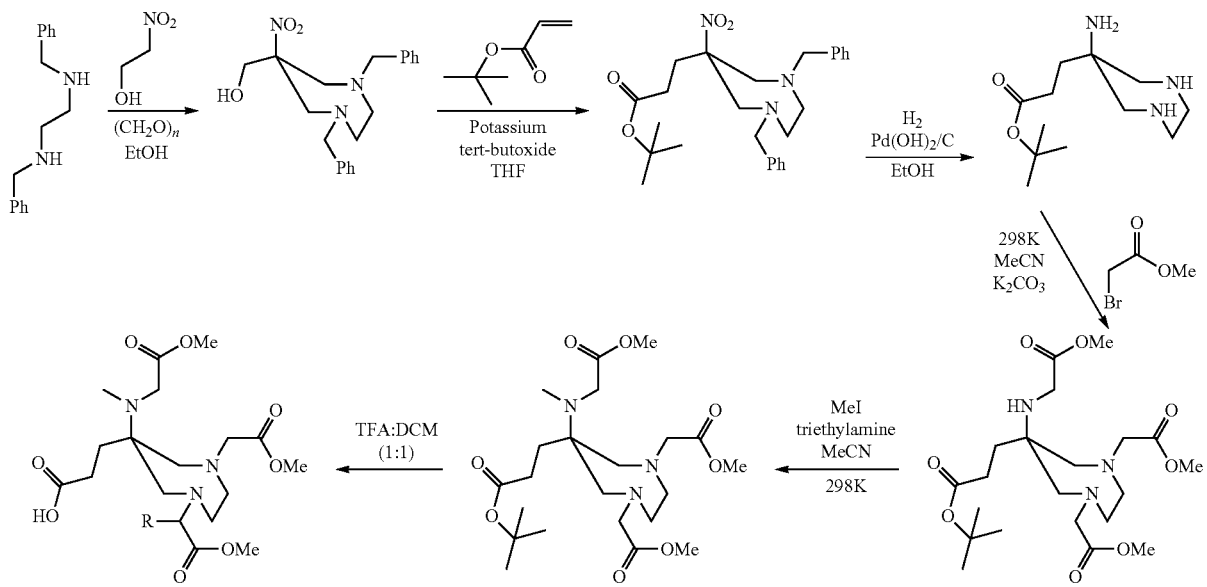

ready for coupling to a TV followed by ester hydrolysis to give the free ligand (OMe converted to OH)

Leads to structures like

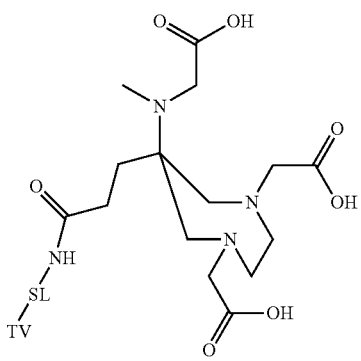

(A.1)

EXAMPLE 9

General labelling procedure applied to radio-label precursors:

A $^{68}Ge/^{68}Ga$ generator was eluted and post processed using the method described by Zhernosekov et al. 400 μL of the $^{68}Ga$ eluate was added to 1 mL of an appropriately prepared buffer solution containing 10 nmol of the chelator. The buffer was selected from either acetate or HEPES depending on the requirements. Buffers were selected according to the pH required for radio-labelling.

pH 4-6:0.2 M acetate buffer pH 6-7:1.0 M HEPES buffer

The reaction progress was monitored by a radio/TLC method using either instant TLC or MERCK silica TLC plates, and eluted using an appropriate mobile phase selected from 0.5 M sodium citrate (pH 4) or 25% EtOH saline (5%) solution. 1 μL of the radio-labelling solution was spotted on the TLC plate at 1, 3, 5 and 10 min intervals following addition of the $^{68}Ga$, and the plate eluted. This allowed the relative amounts of complexed and 'free' 68Ga to be determined. The experiments were performed in triplicate over the pH range 4-7 at room temperature (298 K), 323 and 368 K.

For the ligands shown tested radio-labelling was nearly quantitative and achieved within 10 minutes at room temperature over pH range 4-7. In the pH range 4-6 radio-labelling was >90% after 1 minute, and proceeded to completion within 5 minutes. Subsequent stability studies, indicated that the radio-labelled complexes formed (over the entire pH range tested) were stable and in the presence of apo-transferrin, DTPA, new born calf serum and iron(III) under physiological conditions (pH 7.4 and 310.4 K) for at least 2 hours. As such, they are suitable for in vivo application.

The invention claimed is:

1. A compound C for radio metal complexation comprising a chelator and one or more biological targeting vectors TV conjugated to said chelator, wherein the chelator has structure (C) based on 1,4-diazepine with groups $R_1$, $R_2$, $R_3$, $R_4$, $X_1$, $X_2$, $X_3$;

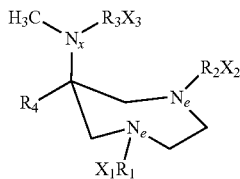

(C)

$X_1$ and $X_2$ are OH;
$X_3$ is OH;
$R_1$, $R_2$ are $CH_2$—CO;
$R_3$ is $CH_2$—CO;
$R_4$ is $CH_3$, $CH(CH_3)_2$, $CH(CH_3)_3$, $(C_6H_5)$, $(C_5H_4N)$, $(C_4H_5NHO)$ or $(C_{(5-k)}H_{(5-k)}N_k)$;
wherein
  $(C_6H_5)$ designates a phenyl ring;
  $(C_{(5-k)}H_{(5-k)}N_k)$ with k=1, 2, 3 or 4 designates a pyrrole, imidazole, triazole or tetrazole residue;
  $(C_4H_5NHO)$ designates a pyrrolidone residue;
  $(C_5H_4N)$ designates pyridine residue;
and
  the one or more targeting vectors TV are conjugated at $R_4$, via optional linker/spacer groups LS, whereby one or more hydrogen atoms of $R_4$ are substituted and
  the one or more targeting vectors TV independently of one another are selected from the group comprising amino acid residues; residues of amino acid derivatives; residues of peptides; residues of Octreotide; residues of proteins; residues of micro proteins; antibodies; recombinant antibodies; antibody fragments; bisphosphonates; sugars; glucose; fructose; sucrose; glutamine; glucosamine; lipids; nucleotides; nucleosides; DNA-components; hypoxia tracers; liposomes; polymers and nanoparticles.

2. A compound C for radio metal complexation comprising a chelator and one or more biological targeting vectors TV conjugated to said chelator, wherein the chelator has structure (B);

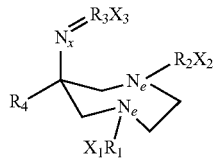

(B)

$R_1$, $R_2$ are $CH_2$—CO;
$R_3$ is CH—CO, CH—POH, CH—POOH, CH—$(C_6H_4)$, CH—$(C_5H_4)$, CH—$(C_{(4-m)}H_{(3-m)}N_m)$, CH—$(C_4H_5O)$, CH—$(C_5H_3N)$—CO, CH—$(C_{(4-p)}H_{(3-p)}N_p)$—CO—, CH—$(C_5H_3N)$—(PH)O or CH—$(C_{(4-p)}H_{(3-p)}N_p)$—(PH)O;

$R_4$ is $CH_3$; and the one or more targeting vectors TV independently of one another are conjugated at $R_1$, $R_2$, $R_3$ and/or at the $CH_2$-residues of the 1,4-diazepine ring via optional linker/spacer groups LS, whereby one or more hydrogen atoms of $R_1$, $R_2$, $R_3$ and/or of the $CH_2$-residues of the 1,4-diazepine ring are substituted.

3. A compound C according to claim 1, wherein the steric bulk value (A-value) of $R_4$ is greater/equal 7.2 kJ/mol.

4. A compound C according to claim 1, wherein the number of atomic bonds along a shortest path between the exocyclic nitrogen $N_x$ and the O-atom of group $X_3$ is 3, 4 or 6.

5. A compound C according to claim 1, wherein the residues of amino acid derivatives are selected from L-tyrosine, L-serine, L-lysine and Alpha-methyl-L-tyrosine; the residues of peptides are selected from bombesins and melanocortins; the antibodies are selected from huKS (humanized antibody for EpCAM respectively KSA) and hu14.18 (humanized antibody for disialoganglioside GD2); the hypoxia tracers are selected from 2-nitroimidazole; azomycine (2-nitroimidazole-arabinoside); erythronitroimidazole; ethyltyrosine; and 2-(2-nitro-(1)H-imidazole-1-yl)-N-(2,2,3,3,3-pentafluoropropyl)-acetamide (EF5).

6. A compound C according to claim 1, wherein one or more targeting vectors TV are conjugated at $R_4$ via linker/spacer groups LS.

7. A compound C according to claim 6, wherein the linker/spacer groups LS independently of one another are residues of molecules selected from the group comprising linear, branched or heterosubstituted, saturated and unsaturated aromatic hydrocarbons of all oxidation states; linear, branched or heterosubstituted alkyls, alkylenes, alkylidenes, aryls, polyethers, polypeptides or sugars.

8. A compound C according to claim 1, wherein said compound (C) is complexed with $^{68}Ga(III)$ and the chelator consists of a 1,4-diazepine derivative.

9. A compound C according to claim 1, wherein the steric bulk of $R_4$ is larger than $N_x$.

10. A compound C according to claim 1, wherein $R_4$ and $N_x$ have an A-value ratio of greater than 8:1.

* * * * *

UNITED STATES PATENT AND TRADEMARK OFFICE
CERTIFICATE OF CORRECTION

PATENT NO. : 10,130,722 B2  
APPLICATION NO. : 14/897142  
DATED : November 20, 2018  
INVENTOR(S) : Frank Rösch et al.

Page 1 of 1

It is certified that error appears in the above-identified patent and that said Letters Patent is hereby corrected as shown below:

In the Claims

Column 31  
Claim 1, Line 17, delete "$R_4$ is $CH_3$, $CH(CH_3)_2$, $CH(CH_3)_3$, $(C_6H_5)$, $(C_5H_4N)$," insert --$R_4$ is $CH_3$, $CH(CH_3)_2$, $C(CH_3)_3$, $(C_6H_5)$, $(C_5H_4N)$,--

Column 32  
Claim 2, Line 4, delete "$CH–(C_5H_3N)–CO$, $CH–(C_{(4-p)}H_{(3-p)}N_p)–CO\ –$," insert --$CH–(C_5H_3N)–CO$, $CH–(C_{(4-p)}H_{(3-p)}N_p)–CO$,--

Signed and Sealed this  
Twelfth Day of February, 2019

Andrei Iancu  
*Director of the United States Patent and Trademark Office*